United States Patent [19]

Kieval

[11] Patent Number: 5,800,464
[45] Date of Patent: Sep. 1, 1998

[54] SYSTEM FOR PROVIDING HYPERPOLARIZATION OF CARDIAC TO ENHANCE CARDIAC FUNCTION

[75] Inventor: Robert S. Kieval, Golden Valley, Minn.

[73] Assignee: Medtronic, Inc., Minneapolis, Minn.

[21] Appl. No.: 720,834

[22] Filed: Oct. 3, 1996

[51] Int. Cl.$^6$ .................................................. A61N 1/365
[52] U.S. Cl. ................................................................ 607/9
[58] Field of Search ........................... 607/5, 7, 9, 11

[56] References Cited

U.S. PATENT DOCUMENTS

| | | | |
|---|---|---|---|
| 4,349,030 | 9/1982 | Belgard . | |
| 4,554,922 | 11/1985 | Prystowsky et al. . | |
| 4,821,723 | 4/1989 | Baker . | |
| 5,018,522 | 5/1991 | Mehra . | |
| 5,087,243 | 2/1992 | Avitall | 604/20 |
| 5,181,511 | 1/1993 | Nickolis . | |
| 5,243,978 | 9/1993 | Duffin, Jr. | 607/11 |
| 5,312,441 | 5/1994 | Mader et al. . | |
| 5,366,485 | 11/1994 | Kroll et al. | 607/5 |
| 5,433,729 | 7/1995 | Adams | 607/5 |
| 5,456,690 | 10/1995 | Duong-Van | 607/5 |
| 5,509,925 | 4/1996 | Adams | 607/5 |
| 5,535,752 | 7/1996 | Halperin et al. | 128/670 |
| 5,564,434 | 10/1996 | Halperin et al. | 128/748 |
| 5,578,062 | 11/1996 | Alf et al. | 607/5 |

OTHER PUBLICATIONS

Direct Current Make & Break Thresholds for Pacemaker Electrodes on the Canine Ventricle Circulation Research vol. XXVII 11–70 pp. 811–823 Nov. 1970.
Virtual Cathode Effects During Stimulation of Cardiac Muscle Circulation Research vol. 68 No.2 Feb. 1991.
Augmentation of Cardiac Output Circulation Research vol. 90 No. 4 PRT 2 Feb. 1991.

*Primary Examiner*—William E. Kamm
*Assistant Examiner*—George R. Evanisko
*Attorney, Agent, or Firm*—Harold R. Patton; Michael B. Atlass

[57] ABSTRACT

An implantable system providing cardiac anodal stimulation (AS) as a system for effecting hyperpolarization of myocardial cells of a heart chamber to enhance the relaxation thereof in the diastolic phase and to thereby enhance cardiac function. The AS system is optimally timed to be delivered in an AS delivery interval following an AS delay interval timed from a preceding ventricular depolarization or pacing pulse to effect maximal cardiac relaxation. The sub-threshold AS pulse or train of pulses is increased in energy (amplitude) and/or decreased in energy to and from a peak energy level gradually rather than abruptly. The AS characteristics are optimized in an initialization process that determines the AS characteristics that provide the optimum blood pressure parameters and thereafter continually or from time to time in a confirmation process. Confirmation of the AS characteristics is determined by measuring one or more blood pressure parameter in the right atrium or ventricle reflecting the blood pressure in the heart chamber subjected to the AS pulses and comparing the measured blood pressure parameter to the corresponding optimum blood pressure parameter determined in the initialization process. The initialization process is repeated if the comparison shows a deterioration in cardiac function response to the AS. The AS pulse waveforms are preferrably delivered through a plurality of discrete AS electrodes distributed about the heart chamber or through or large surface area epicardial patch or endocardial AS electrodes.

20 Claims, 14 Drawing Sheets

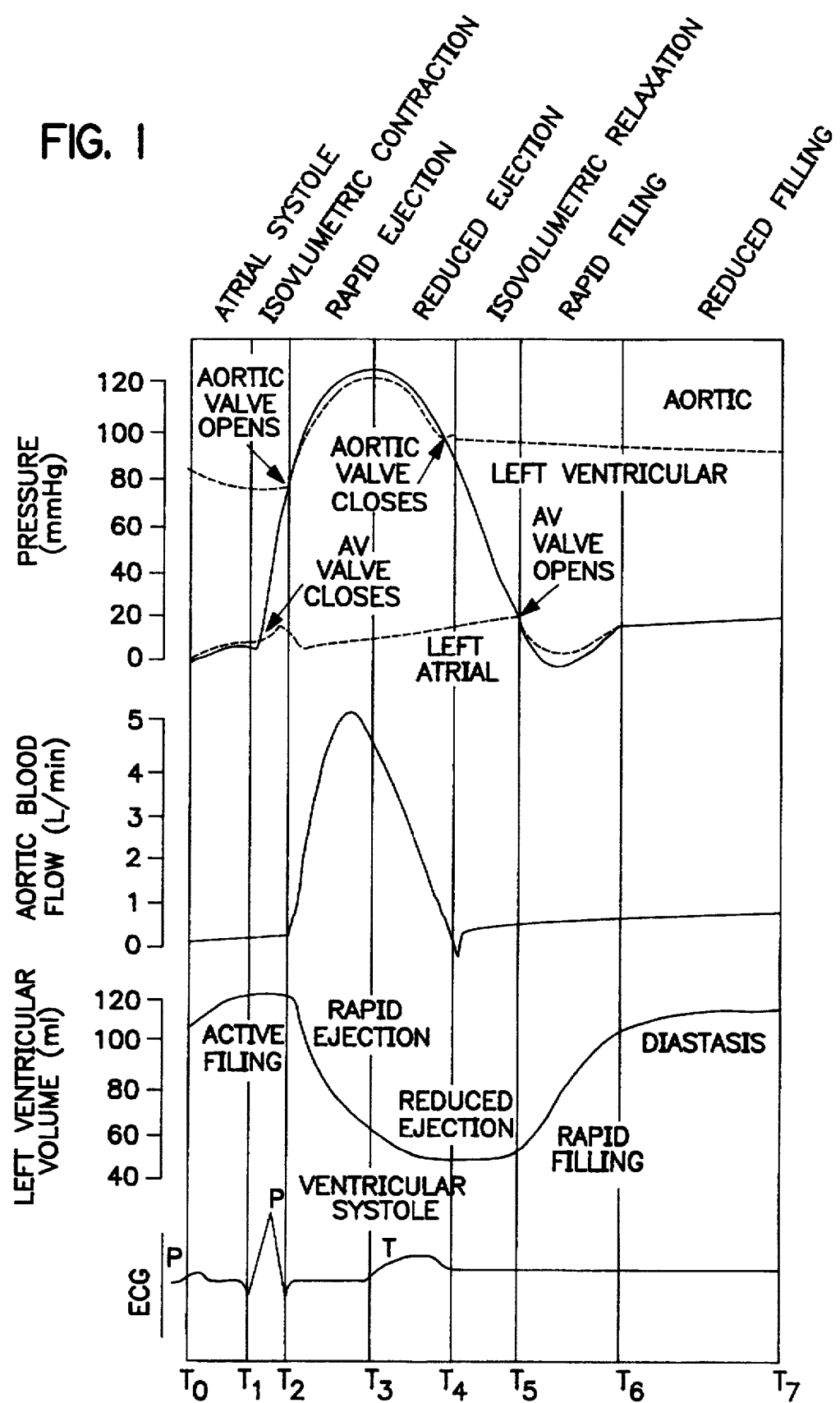

SYSTEM FOR PROVIDING HYPERPOLARIZATION OF CARDIAC TO ENHANCE CARDIAC FUNCTION

CROSS-REFERENCE TO RELATED APPLICATIONS

Reference is hereby made to commonly assigned, co-pending U.S. patent application Ser. No. (08/720,886) filed on even date herewith for CARDIAC ARRHYTHMIA MANAGEMENT BY APPLICATION OF ANODAL STIMULATION FOR HYPERPOLARIZATION OF MYOCARDIAL CELLS in the name of Robert S. Kieval, VMD, Ph.D and Ser. No. 08/640,046 (P3787) filed Apr. 30, 1996, for ATRIAL FIBRILLATION PREVENTION PACING SYSTEM by Rahul Mehra.

FIELD OF THE INVENTION

The present invention relates to an implantable system for providing cardiac anodal stimulation (AS) for the augmentation of cardiac function and particularly to the use of anodal stimulation energy for effecting hyperpolarization of myocardial cells of a heart chamber to enhance the relaxation thereof in the diastolic phase and to thereby enhance cardiac function.

BACKGROUND OF THE INVENTION

In the infancy of heart pacing stimulators, there were experiments using various forms of electrical stimulation pulses including anodal (positive going) and cathodal (negative going) pacing pulses having pulse energy exceeding the stimulation threshold to trigger depolarization of myocardial cells. During electrical stimulation of the heart using bipolar electrodes, myocardial cells in the region of the anodal electrode become hyperpolarized, while cells near the cathodal electrode become depolarized. During unipolar anodal stimulation, myocardial activation is in part accomplished through break excitation of myocardial cells near the anode electrode following the cessation of the hyperpolarizing stimulus.

Early studies were conducted to determine if the optimum stimulation pulse polarity and wave shape could be found that would achieve capture of the heart at the lowest expenditure of pulse energy in order to prolong pacemaker battery life as reported, for example, by Egbert Dekker, M.D., in "Direct Current Make and Break Thresholds for Pacemaker Leads", (*Circulation Research*, vol. XXVII, November 1970, pp. 811–823). Contemporaneously, attention was focused on other factors, particularly high energy density, low self discharge, battery technology, pacing electrode materials, surface areas, and configurations, variable pulse energy output pulse circuits, and capture threshold determination techniques, that made dramatic improvements in pacemaker implantable pulse generator (IPG) longevity, reliability and size. After this experimental period the exponential decaying voltage, cathodal (negative going) pacing pulse shape achieved by a relatively simple, monophasic capacitive discharge output circuit became accepted as the standard in pacemaker IPG technology.

Meanwhile, in the field of external temporary pacemakers for pacing the heart through electrodes placed in contact with the patient's chest, effort has continued to the present time to determine a pacing pulse type and shape, including amplitude, width and wave shape, that causes the least amount of pain to the patient. In this case, energy consumption of battery powered temporary pacemakers is of less importance since the battery may readily be changed when a warning of impending depletion occurs. In order to capture the heart through the skin and body tissue, it is necessary that the applied pacing pulse energy be several orders of magnitude higher than that necessary to capture the heart with pacing pulses applied through state of the art pacing leads in contact with the heart. In order to reduce pain to the patient, the energy is spread out in long duration, typically anodal (positive going), constant current pulses that are ramped up at the leading edge to the constant current plateau and then are ramped down at the trailing edge. Such anodal wave shapes and pulse generating circuits are apparently more comfortable than cathodal wave shapes and are disclosed in commonly assigned U.S. Pat. Nos. 5,018,522 and 4,349,030, for example.

Returning to the implantable pacemaker pacing pulse polarity, more recently, Hummel et al., in "Augmentation of Cardiac Output by Anodal Pacing", *Circulation*, Vol. 90, No. 4, Part 2, P. I-69, (1994) compared cardiac output (CO) resulting from stimulation with cathodal and anodal, capacitive discharge, pacing pulses of otherwise identical specifications and found a 10% improvement in CO using anodal stimulation. This result is attributed to hyperpolarization of the tissue prior to its excitation and an increase in calcium release upon the subsequent depolarization of the cell. This data suggests that systolic function could be improved by anodal pacing pulses. Alternatively, the improvement in CO could be related to an improvement in diastolic function. However, the effects of anodal pacing on diastolic function were not studied. Ultimately, in my view, both mechanisms may have contributed to the observed result.

In the field of implantable arrhythmia control devices, considerable effort has been expended in applying electrical stimulation regimens to the heart to inhibit or correct tachyarrhythmias including high rate atrial and ventricular tachycardia and fibrillation and atrial flutter. Tachyarrhythmias are episodes of inappropriate, high rate, cardiac depolarizations, and are distinguished from sinus tachycardias that physiologically accompany exercise to provide adequate CO. Tachyarrhythmias that are sufficiently high in rate or chaotic compromise CO from the affected chamber (s), leading to loss of consciousness and death, in the case of ventricular fibrillation, or weakness and dizziness, in the case of atrial fibrillation or flutter and non-sinus atrial and ventricular tachycardias. Atrial fibrillation and flutter are debilitating, due to the loss of atrial contribution and interference with ventricular filling, but not immediately life threatening unless it leads to ventricular arrhythmias or stroke.

Over the years, considerable interest has been shown in applying multiple pace/sense electrodes distributed about the heart either within the heart chambers or outside the heart chambers in order to determine the nature of arrhythmias from the timing of depolarizations detected at each electrode or deliver pacing pulses simultaneously or in particular timed sequences to the electrodes. In U.S. Pat. No. 4,554,922, a system is proposed for applying "conditioning", varying energy, pulses to a number of such electrode sites following the refractory period in order to either inhibit the development of or terminate a tachyarrhythmia. In U.S. Pat. No. 5,181,511, a system is disclosed for applying anti-tachycardia pacing therapies to an affected heart chamber using a "virtual electrode" approach of a multitude of electrodes arranged inside the right atrium or ventricle or on the epicardium for determining the focus site of origin of the tachycardia and for delivering the therapy in a timed fashion. The above-referenced patent application Ser. No. 08/640,046 describes details of a system for applying pacing pulses to a number of electrode pairs distributed about the heart. In such systems, cathodal pacing energy pulses or sub-threshold stimulation pulses are applied to the multiple electrode sites.

Recently, implantable cardiac pacing employing dual chamber, cathodal, pacing pulse stimulation therapies have been investigated as a therapy for congestive heart failure (CHF). CHF and other pathological conditions of the heart, including hypertensive heart disease and cardiomyopathy, may involve not only systolic dysfunction, characterized by depressed contractility, but significant diastolic dysfunction as well, manifested as impaired myocardial relaxation and ventricular chamber filling in the diastolic phase following a contraction. The pulmonary congestion and compromised stroke volume associated with diastolic dysfunction contribute to patient symptoms of exertional dyspnea and exercise intolerance. In the up to 30% of CHF patients with normal systolic function, such symptoms are attributed to diastolic dysfunction alone. In patients with heart failure, the New York Heart Association Functional Class correlates more closely with the degree of diastolic dysfunction than with the severity of systolic dysfunction. Finally, abnormalities in Doppler-derived indices of left ventricular diastolic function are predictive of higher cardiac mortality and thus contribute to the poor prognosis of heart failure patients.

The cellular pathophysiology of diastolic dysfunction is thought to involve, in part, abnormal calcium handling by diseased cardiac myocytes. In pathologically depolarized myocardial tissue, cell calcium may be elevated due to opening of voltage dependent calcium channels resulting in inward calcium flux. In addition, diastolic sequestration and extrusion of calcium ions may be retarded, even in non-depolarized cells, also leading to persistent elevation of cytosolic calcium concentration. These deficits result in incomplete relaxation of myofilaments and higher resting tension. The cellular calcium overload has also been implicated in cardiac arrhythmogenesis. While pharmacological therapy for myocardial disease may focus on improving systolic function (e.g., with the use of positive inotropic agents), ameliorating diastolic function (e.g., with calcium channel blockers to reduce cell calcium levels, which also exerts an anti-arrhythmic effect), is also an important therapeutic strategy.

Patients suffering from these conditions often manifest other cardiac arrhythmic conditions that may make them suitable candidates for cardiac pacing therapies including demand pacing for bradycardia and high rate or burst anti-tachycardia pacing therapies. Single and dual chamber demand pacing therapies have long been prescribed for patient's whose heart rates provide insufficient CO. The conventional implantable cardiac pacemaker includes an implantable pulse generator (IPG) coupled with a lead system having a cathodal stimulation electrode and a return or indifferent electrode. Implantable defibrillators, some of which also provide a pacing function could also be used for this invention.

The use of pacing therapies for these conditions has largely centered on augmenting systolic function of the heart, as reflected by increased CO or ejection fraction. While these pacing therapies may maximize ventricular filling and minimize atrio-ventricular (AV) valvular regurgitation by optimizing AV mechanical synchrony, the use of anodal stimulation specifically to improve the relaxation process in the heart, and thus to further relieve patient symptoms and potentially improve prognosis, without capturing the heart, has not, to the best of my knowledge, been reported. Consequently, a need exists for an implantable system for improving cardiac function in such patients and also for improving the cardiac function of more typical patients treated with implantable pacemakers or defibrillators.

SUMMARY OF THE INVENTION

It is therefore an object of the present invention to provide a system for augmenting cardiac function in such patients requiring increased CO through the use of an Anodal Stimulation(AS) system which generates and is constructed to deliver pulses or pulse trains to hyperpolarize myocardial cells preferrablyduring the relaxation phase of the cardiac cycle.

Accordingly, a system for augmenting cardiac function is envisioned comprising an AS system generator and one or more AS electrodes distributed over the endocardial surface and/or epicardial surface of the heart chamber for providing anodal stimulation timed to an appropriate point in the cardiac cycle, with an appropriate stimulus intensity, to hyperpolarize large portions of the myocardium of that heart chamber. The present invention may be implemented in an IPG and lead system timing the delivery of the AS pulses to atrial and/or ventricular depolarizations of the heart or in conjunction with a pacing system for triggering the depolarizations, if necessary. The AS system is optimally timed to be delivered in an AS delivery interval following an AS delay interval timed from a preceding ventricular depolarization or pacing pulse to effect maximal cardiac relaxation.

The AS system characteristics include the AS delay and delivery intervals, the stimulation pulse type, shape, and energy. To avoid make or break excitation of myocardial cells when the hyperpolarizing anodal therapy is initiated or terminated, the AS pulse or train of pulses is preferably increased in energy (amplitude) and/or decreased in energy to and from a peak energy level gradually rather than abruptly.

A variety of electrode configurations may optimally be employed to distribute the AS pulses over a wide area or volume of myocardial cells including atrial and ventricular pacing electrodes, large surface area epicardial or intracardiac electrodes and return electrodes including one or more such electrodes or a remote electrode, e.g., the exposed external surface of the IPG.

The AS pulse characteristics are preferably optimized in initialization and/or maintenance or adjustment processes that determine the AS pulse's characteristics that provide the optimum blood pressure parameters and thereafter continually or from time to time in a confirmation process. The confirmation of the AS pulse characteristics is preferably determined by measuring one or more blood pressure parameter in the right ventricle reflecting the blood pressure in the heart chamber subjected to the AS system and comparing the measured blood pressure parameter to the corresponding optimum blood pressure parameter determined in the initialization process. The initialization process is repeated if the comparison shows a deterioration in cardiac function in response to the delivery of electrical pulses by an AS system. Any other parameter and sensor used to estimate CO (again, this term means Cardiac Output) or cardiac function such as for example how quickly ventricular pressure is falling or RV diastolic absolute pressure or mixed venous Oxygen saturation, catecholamine level, QT interval, Heart Rate and any number of other indicators alone or in combination as may be known to those of skill in determining CO or cardiac function level would recognize, may be used. For my preferred embodiment I prefer RVpressure since sensors for this are already well defined.

A number of advantages are believed to flow from the use of the method and apparatus of the present invention in an implanted system. When resting myocardial cells are hyperpolarized, the increase in membrane potential results in further relaxation, as evidenced by cell elongation, which presumably reflects a reduction in the cytosolic free calcium concentration possibly secondary to enhanced sarcolemmal sodium-calcium exchange. In the intact heart, hyperpolarization of myocardial cells or repolarization of cells which are pathologically depolarized may also be expected to reduce cell calcium levels, either through augmented sodium-calcium exchange or internal sequestration, or inactivation of voltage-dependent calcium channels, respectively. Thus, in my view, having the ability to hyperpolarize large regions of myocardium can provide improvment in myocardial relaxation and ventricular performance. The drop in cell calcium levels accompanying hyperpolarization may also reduce the incidence of cardiac arrhythmias related to cellular calcium overload. In addition, the control of cell membrane potential by stimulation that hyperpolarizes the myocardium may control or prevent aberrant cardiac electrical activity such as retrograde conduction and other arrhythmic conditions. This approach can also be very attractive as an anti-arrhythmic technique, as it could avoid the need for painful, debilitating, and potentially damaging high intensity depolarizing electrical shocks, as described in the above-referenced (08/720,886) application, filed on even date herewith.

BRIEF DESCRIPTION THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is a schematic illustration of the cardiac cycle in which the delivery of an AS pulse is intended to be timed to be delivered within the intrinsic relaxation period between natural or pace-triggered depolarizations to effect hyperpolarization of heart cells;

FIGS. 2A–C are examples of timing diagrams:

FIG. 3 is an illustration of a first embodiment of an IPG and lead system for delivering AS to the heart employing virtual electrodes in conjunction with the detection and processing of the right ventricular blood pressure;

FIG. 4 is a system block diagram illustrating the components of an implantable pulse generator for generating and delivering AS pulses in one or more of the illustrated waveforms and cardiac pacing to one or both chambers of the heart using alternative electrode systems described herein and optionally including a system for optimizing the delivery characteristics of the AS pulses as a function of intracardiac blood pressure;

DETAILED DESCRIPTION OF THE PREFERRED EMBODIMENTS

Figure 2A:
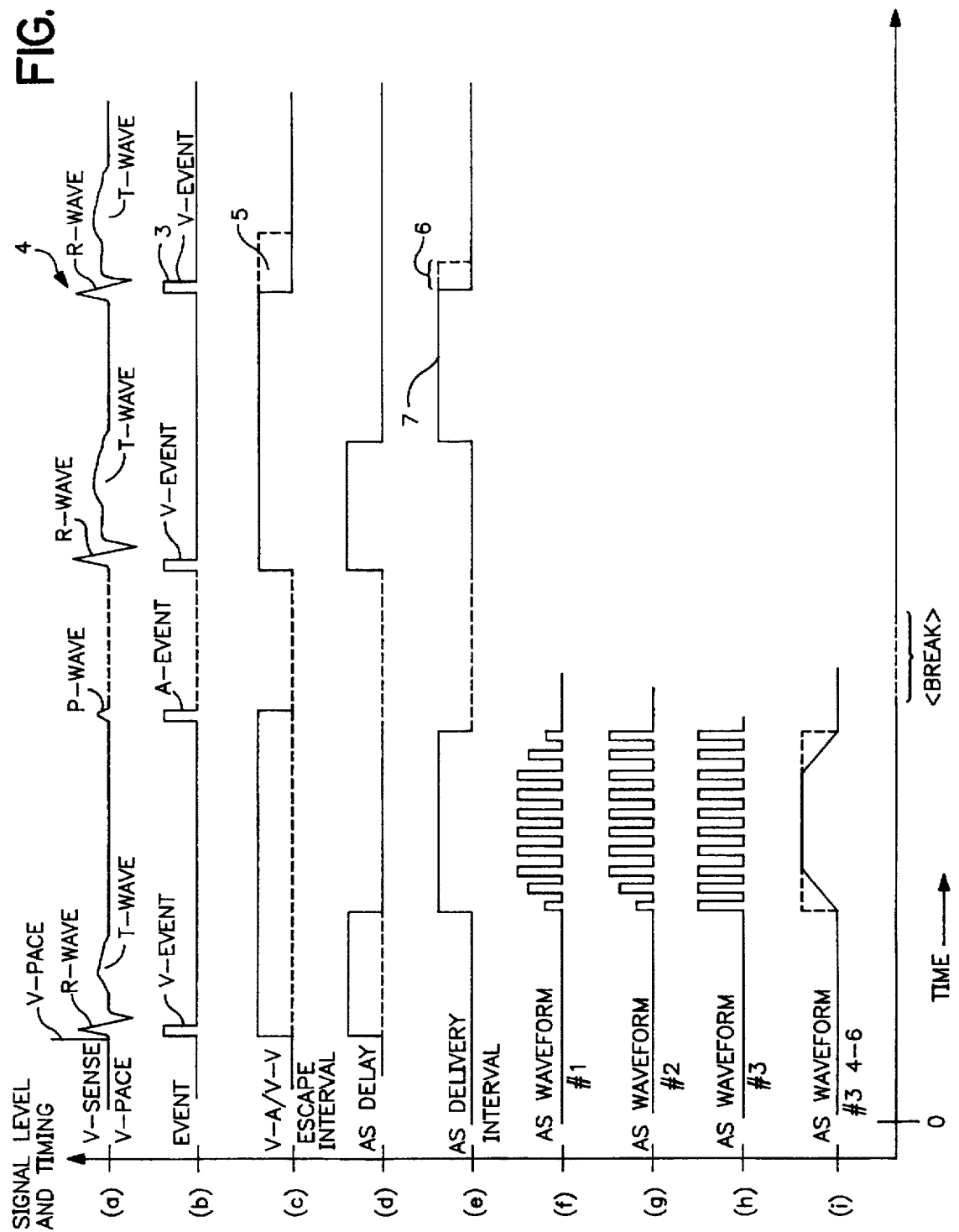

Before describing the inventive method and apparatus embodied in the preferred systems, attention is directed to FIG. 1 that depicts the electrical depolarization waves attendant a normal sinus rhythm cardiac cycle in relation to the fluctuations in absolute blood pressure, aortic blood flow and ventricular volume in the left heart. The right atria and ventricles exhibit similar pressure, flow and volume fluctuations in relation to the PQRST complex. The cardiac cycle is completed in the interval between successive PQRST complexes and following relaxation of the atria and ventricles as the right and left atria re-fill with venous blood and oxygenated blood. In sinus rhythm, the interval between depolarizations may be on the order of 500.0 ms to 1,000.0 ms for a corresponding sinus heart rate of 120 bpm to 60 bpm, respectively. In this time interval, the atria and ventricles are relaxed, and overall atrial size or volume may vary as a function of pleural pressure and respiration. In the blood pressure diagrams of FIG. 1, it may be observed that the atrial and ventricular blood pressure changes track and lag the P-waves and R-waves of the cardiac cycle. The time period $T_0$–$T_1$ encompasses the AV interval.

In patients suffering from cardiac insufficiency arising from bradycardia due to an incompetent SA node or AV-block, atrial and/or ventricular conventional pacing may be prescribed to restore a sufficient heart rate and AV synchrony. In FIG. 1, for example, atrial and/or ventricular pacing pulses would precede the P-wave and the downward Q deflection of the PQRS complex commonly referred to as the R-wave. However, CO effected by the contraction following the atrial and/or ventricular pacing pulse may be constrained by the inability of the atrial or ventricular myocardial cells to relax during the period of isovolumetric relaxation and the following periods of rapid and reduced, passive filling phase between $T_4$–$T_7$ as well as during atrial systole time period $T_0$–$T_1$ shown in FIG. 1. Thus, the amount of blood expelled from the atria and/or ventricles in the next cardiac cycle may be less than optimum. This is particularly the case with CHF patients or other patients in whom the stiffness of the heart is increased, significantly limiting cardiac filling during the passive filling phase between $T_4$–$T_7$ as well as during atrial systole time period $T_0$–$T_1$.

Turning to FIG. 2, the timing diagram illustrates the timing of delivery of AS energy to the heart in relation to a timed interval from a sensed or paced event as well as alternative pulse waveforms of the anodal stimulation. In accordance with the present invention, an AS pulse or pulse train is delivered to the atria and/or ventricles in the depicted time intervals. Turning first to the illustrated pulse waveforms of tracings (e)–(i), the AS therapies are intended to be sub-threshold in nature, that is, of insufficient energy to depolarize the myocardial cells and/or shaped to avoid depolarizing the myocardial cells due to make or break excitation effects. Consequently, the delivery of these AS therapies presents issues including how to distribute the sub-threshold energy to an appreciable mass of hyperpolarized myocardial cells to facilitate relaxation and refilling of the chamber with blood without causing depolarization to occur or triggering an arrhythmia.

The delivery of the AS pulse or pulse train should be over an appreciable area or volume of myocardial cells in order to attain the advantages thereof. In one stimulation approach, Wikswo et al. in "Virtual Cathode Effects During Stimulation of Cardiac Tissue" (*Circulation Research*, Vol. 68, No. 2, February, 1991, pp.. 513–530), have described a virtual cathode effect whereby application of supra-threshold cathodal stimuli to the epicardium results in initial simultaneous activation of a region of myocardium with dimensions larger that those of the physical cathode electrode. Exploiting this effect during anodal stimulation can minimize the number and/or size of electrodes needed to control myocardial membrane potential so that conventional or near conventional cardiac pacing leads could be used. Alternatively, it is contemplated that one or more large epicardial patch defibrillation electrodes or any of the intracardiac, large surface area, defibrillation electrodes similar to those well known in the art could be used to distribute the anodal stimulation. Additional variations include the distributed sets of pairs of bipolar electrodes described below or distributed unipolar electrodes such as are disclosed in the above-referenced 5,181,511 patent.

Turning to the timing of delivery and alternative forms of the AS therapies illustrated in the timing and signal chart of signal level tracings illustrated in FIGS. 2A and B, either a single anodal pulse or a burst or train of constant or variable frequency pulses may be delivered to brung about the hyperpolarized state in tissue. Example pulse waveforms are illustrated in tracings (e)–(i) in FIG. 2A and (e) of 2B. The FIG. 2A timing illustrates how the invention can be used for ventricular tissue hyperpolarization and the 2B chart is for Atrial tissue. Generally a pace or a sensed event such as V-Sense and V-Pace in FIG. 2A (tracing (a)) cause a signal to be generated in a cardiac monitoring circuit in a pacemaker or similarly situated device to cause the V-event signals such as those illustrated in the (b) tracing in the FIG. 2A to be generated. Such a signal is generally available to the device to generate escape interval timing and delay timing signals, either of which can be used to trigger the initiation of the delivery of the hyperpolarization pulse waveforms. Preferably, an AS delivery time interval (tracing (e)) after time-out of an AS delay interval (tracing (d)) from a preceding ventricular sense or pace event (tracings (a) and (b)) can be used to time the beginning and termination of the hyperpolarization waveform delivery. Ventricular events are chosen in order to time the delivery of the anodal stimulation energy to the selected heart chamber or both heart chambers during the relaxation phase of the cardiac cycle illustrated in FIG. 1. The ventricular sense or pace event detected in tracing (b) also triggers the timing out of an escape interval in tracing (c) which may be terminated by the sensing of a subsequent atrial or ventricular event, depending on the operating mode of the system. The first depicted sequence in FIG. 2A shows the full time-out of the escape interval in tracing (c) and the AS delay and delivery intervals in tracings (d) and (e). The AS delay and delivery intervals can be set to be completed within the escape interval and may be derived as a function of an intrinsic V-V or V-A escape interval derived by measuring and averaging intervals between intrinsic ventricular and/or atrial sense events or paced events. As illustrated, the AS delay interval delays delivery of the AS pulse or pulse train until after expiration of an excitable phase of the heart, i.e., after the T-wave which follows an intrinsic or pace evoked R-wave. The AS delivery interval is timed to time-out before the end of the previously derived V-V or V-A escape interval. If the invention were to be used in a purely atrial chamber device or to also have an atrial chamber hyperpolarization electrode system, the illustrated tracings of FIG. 2B should be used as a guide to implementation of this invention. Here the timing stems from the A-Sense (P-wave or Apace signal). If preferred, a signal other than A-A interval could be used, such as V-A interval if desired. Note that the tracing (f) of FIG. 2B can take on the same or similar characteristics to those illustrated in FIGS. 2A(f–i), if desirable.

In the first illustrated case In FIG. 2A, the escape interval terminates in response to the sensing of a P-wave after the time-out of the AS delivery interval. In the second illustrated case, at the right side of FIG. 2A, the premature sensing of a qualified sense event 3, in this case an R-wave 4, should be acted upon by the device to terminate the AS delivery time interval (thus eliminating the unused temporal portion 6 of AS delivery interval 7. This can be handled in various ways by the device, a typical pacemaker shrinking the escape interval as in area 5 although many techniques may be used as is known to those of skill in this art.). If a sense event occurs earlier during the time-out of the AS delay interval, then the timing should be reset to restart the AS delay interval for the next heart cycle. This same feature should be implemented in the atrium if one is using a hyperpolarization AS system in the atrium, but in such systems, the truncation should be based on a PAC rather than a PVC as just illustrated.

The AS stimulation energy may be delivered in the form of a single pulse of constant amplitude as shown in tracing (i) or as a burst of constant energy stimulation pulses. With respect to avoidance of leading or trailing edge effect excitation leading to depolarization of myocardial cells (called "break excitation"), the leading and/or trailing edges of the AS pulse or pulses of tracings (f)–(i) preferably have ramped amplitudes similar to the illustration. In tracings (f) and (g) the ramp up leading edge amplitudes of a sub-set of the pulses of the burst are shown increasing from an initial amplitude to a maximum amplitude. In tracings(f) and (h) the ramp down trailing edge amplitudes of a further sub-set of the pulses of the burst are shown decreasing from the maximum amplitude to a terminating amplitude. In tracing (i), the ramp up leading edge and ramp down trailing edge waveforms between the initial amplitude, the maximum amplitude and the terminating amplitude are shown in dotted lines.

The present invention is preferably implemented into a system that may include conventional pacing therapies and operating modes or as a stand alone system for simply providing AS pulse therapies to effect hyperpolarization of myocardial cells between sensed PQRST complexes as shown in FIG. 2A. In addition, such a system may include a blood pressure sensor for measuring the blood pressure in the cardiac chamber of interest and optimizing the pressure through the timing of delivery of the AS pulse or pulse train in a feedback algorithm. Of course alternative sensors or combinations of sensors may be used as mentioned above for determination of CO or cardiac function, but I prefer the pressure sensor presently because of its availability and stability.

Figure 3:
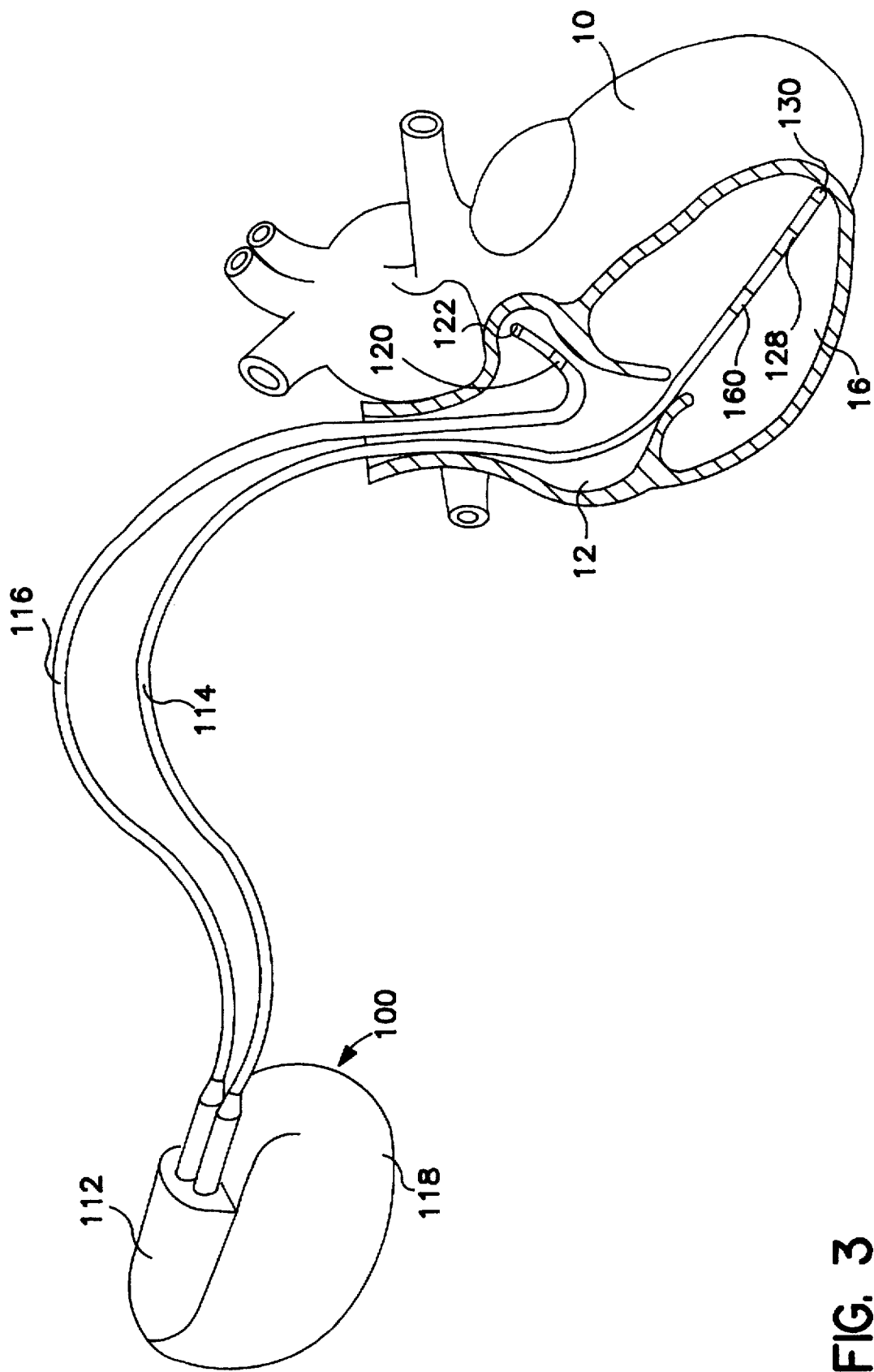

Turning now to FIG. 3, depicting the external configuration of such a system, preferably a dual chamber implantable pulse generator (IPG) 100, which is provided with a hermetically sealed enclosure, preferably fabricated of a biocompatible material, the most common of which is currently the metal titanium, but other materials are known and could obviously be used. A connector block assembly 112 (also of a bio-compatible material, in this case preferrably a plastic) receives electrical connectors located on the proximal ends of unipolar or bipolar leads 114 and 116 (bipolar leads are depicted) for making electrical connection with the circuitry within the enclosure. The combination of the leads 114 and 116 and the IPG 100 may constitute an implantable dual chamber pacemaker, e.g. a DDD or DDDR pacemaker, additionally incorporating the features of the present invention. In accordance with one implementation of the present invention, the enclosure may be employed as a further can electrode 118 during delivery of the AS pulses to effect hyperpolarization as described below. A pressure sensor 160 may be mounted to the lead 114 or 116 in order to derive an absolute or rate of change blood pressure signal that may be used in a manner described below to optimize the timing of delivery of the AS pulses. If the reader is using other sensors or testing CO or cardiac function with other means, he should adopt the appropriate location and measurement cycle for those means chosen to remain within the scope of this invention.

Atrial lead 116 is an atrial bipolar pacing lead, carrying two electrodes 120 and 122. Electrodes 120 and 122 are used both to sense P-waves and to deliver atrial pacing (a-PACE) pulses. Atrial pacing pulses may be delivered between electrodes 120 and 122 in a bipolar pacing mode or between electrode 122 and the housing 118 of the IPG 100 in a unipolar pacing mode. Sensing of P-waves may occur between electrode 120 and electrode 122 in a bipolar sensing mode or between either of electrode 120 and 122 and the can electrode 118 of the IPG 100 in a unipolar sensing mode.

Similarly, ventricular lead 114 represents a ventricular bipolar pacing lead, carrying two electrodes 128 and 130 that are used to sense R-waves and apply V-PACE pulses to the ventricle. Bipolar ventricular pacing may be accomplished between electrodes 130 and 128, or unipolar ventricular pacing may be accomplished between electrode 130 and the conductive can electrode 118. Sensing of R-waves may also be accomplished between electrodes 130 and 128 in a bipolar sensing mode or between either of electrodes 130 and 128 and the can electrode 118 of the IPG 26 in a unipolar sensing mode.

The IPG 100 is preferably, but not necessarily, capable of operating in a DDD or DDDR dual chamber pacing mode or in a single chamber pacing mode. (Alternatively, of course, this invention could be implemented in devices that only deliver AS pulses if desired or that provide some other function, such a s delivery of drugs, stimulation to reduce or eliminate pain, guard against fibrillation by delivering defibrillating pulses, and so on as is appropriate to the particular patient. I illustrate my invention with the IPG 100 as a first preferred embodiment only.) In the DDD or DDDR modes, A-PACE and V-PACE pulses are delivered to right atrium 12 and right ventricle 16 in AV synchrony, and sensed P-waves and R-waves are both effective to inhibit delivery of the next scheduled pacing pulse in the chamber in which they are detected or in any related mode where the AV delay interval is employed, including the related DDI, DVI, DVIR and DDIR modes. However, as stated above, the present invention may also be implemented into a non-pacing system that does not provide any conventional pacing functions or provides additional functions as mentioned in the parenthetical above in this paragraph. The system of FIG. 3 is intended to depict the comprehensive dual chamber pacing system as well as the components of the single chamber pacing systems and the non-pacing system with or without the blood pressure sensing system.

In accordance with a first aspect of the present invention, the AS therapies illustrated in FIG. 2 may be applied between each of the atrial and/or ventricular electrodes 120, 122, 18, 130 employed in the particular system using the can electrode 118 as a return electrode. The virtual electrode effect provides for distribution of the AS system energy over a larger area than simply the myocardial cells in contact with the electrodes and hyperpolarization of the affected cells.

Figure 4:
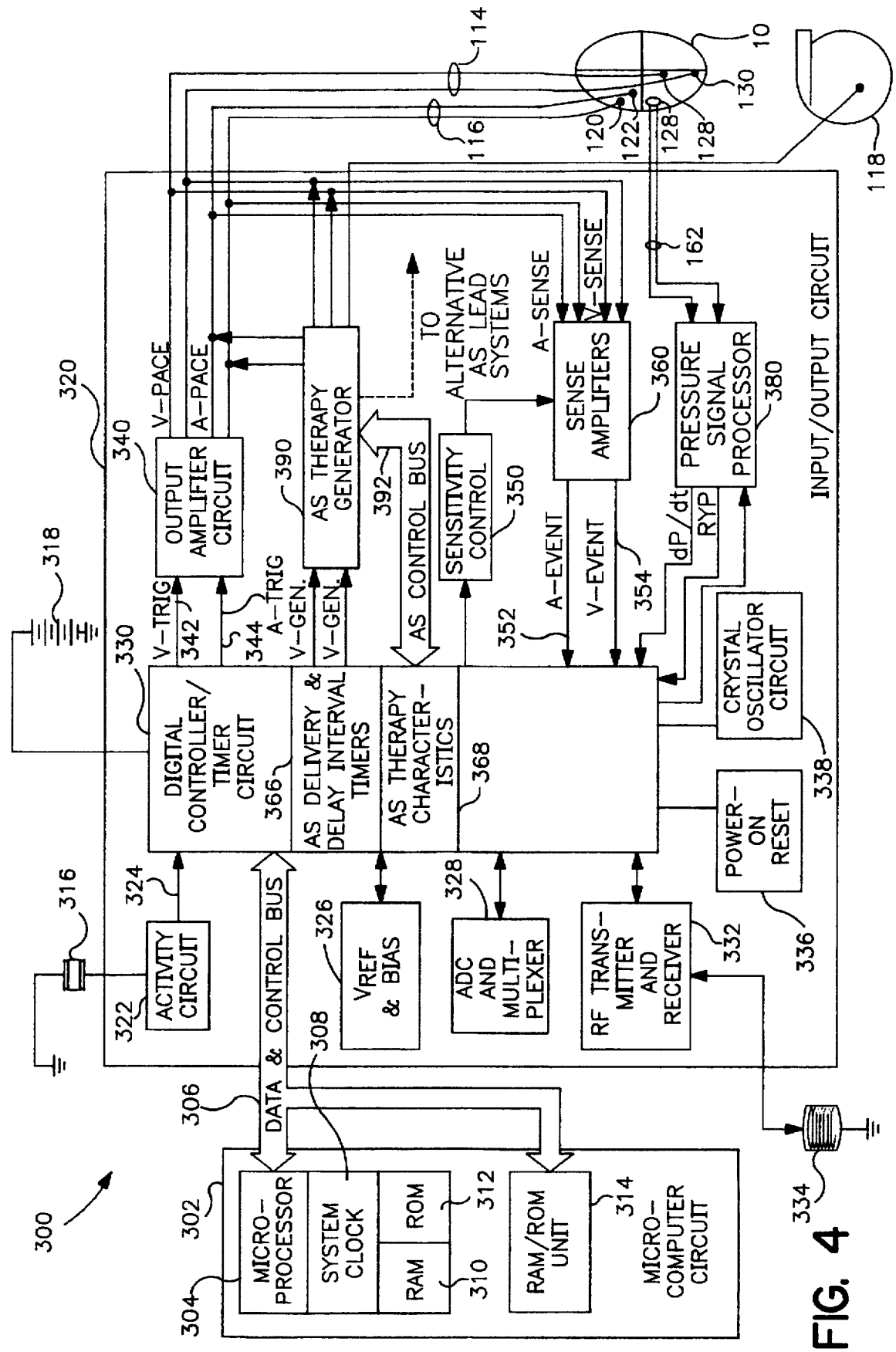

Turning now to FIG. 4, it depicts a DDDR IPG circuit 300 and atrial and ventricular leads 114, 116, can electrode 118, and pressure sensor 160 in relation to the heart 10. The IPG circuit 300 is divided generally into a microcomputer circuit 302 and a pacing circuit 320 interconnected by a data and control bus 306. The pacing circuit 320 includes the output amplifier circuit 340 and the sense amplifier circuit 360, as well as a pressure signal processor 380 and a number of other components described below. The output circuit 340 and sense amplifiers circuit 360 may contain pulse generators and sense amplifiers corresponding to any of those presently employed in commercially marketed cardiac pacemakers for atrial and ventricular pacing and sensing.

Bipolar leads 114 and 116 are illustrated schematically with their associated electrode sets 120, 122 and 128, 130, respectively, as coupled directly to the input/output circuit 320. Similarly, the right ventricular absolute pressure sensor 160 is schematically shown in the right ventricle 16 at the end of a further lead conductor pair 162 (that may or may not be incorporated into ventricular lead 114) and shown directly connected to the pressure signal processor 380. However, in the actual implantable device they would, of course, be coupled by means of removable electrical connectors inserted in connector block assembly 112 of FIG. 3.

P-waves in the A-SENSE signal that are sensed by the atrial sense amplifier result in an A-EVENT signal that is communicated to the digital controller/timer circuit 330. Similarly, R-waves in the V-SENSE signal are sensed by the ventricular sense amplifier result in a V-EVENT signal that is communicated to the digital controller/timer circuit 330. The pressure signal processor 380 develops a right ventricular absolute blood pressure signal RVP and/or rate of change blood pressure signals +dP/dt and/or −dP/dt that are provided to the digital controller/timer circuit 330.

In order to trigger generation of a ventricular pacing or V-PACE pulse, digital controller/timer circuit 330 generates a V-TRIG signal at the end of an AV delay provided by AV delay interval timer 372. Similarly, in order to trigger an atrial pacing or A-PACE pulse, digital controller/timer circuit 330 generates an A-TRIG signal.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

Data transmission to and from the external programmer of the patient communications control device of the present invention is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art. Such data transmission could also include status of AS parameters, including measures of responsiveness to AS delivery currently or over time.

In the preferred embodiment a microcomputer circuit 302 is included in the housing and contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-TRIG, V-TRIG, pace initiating signals and A-EVENT and V-EVENT sense or occurrance indicator signals. The specific values of the intervals defined are controlled by the microcomputer circuit 302 by means of data and control bus 306 from programmed-in parameter values and operating modes.

Control of timing and other functions within the pacing circuit 320 can be provided by controller/timer circuit 330, operating under the general control of the microcomputer 302, which includes a set of timing and associated logic circuits of which certain ones pertinent to the present invention are depicted, including AS delay and delivery interval timers 366. Other timing circuits include an atrial interval timer for timing elapsed V-A intervals, escape interval timers for timing A-A, V-A, and/or V-V pacing escape intervals, an AV delay interval timer for timing an AV delay from a preceding A-EVENT or A-TRIG and an anodal hyperpolarization delivery interval timer 366. Microcomputer 302 can control the operational functions of controller/timer 324, specifying which timing intervals are employed, and setting programmed-in base timing intervals, via data and control bus 306.

Digital controller/timer circuit 330 starts and times out these intervals for controlling operation of the atrial and ventricular sense amplifiers in sense amplifier circuit 360 and the atrial and ventricular pace pulse generators in output amplifier circuit 340 in accordance with the flowchart of FIG. 5 described below. Typically, depending on the operational pacing mode, digital controller/timer circuit 330 also defines associated intervals including an atrial blanking interval following delivery of an A-TRIG pulse or V-TRIG pulse, during which atrial sensing is disabled, as well as ventricular blanking intervals following a V-TRIG atrial pulse, during which ventricular sensing is disabled. Digital controller/timer circuit 330 also defines an atrial refractory period (ARP) during which atrial sensing is disabled or the A-EVENT is ignored for the purpose of resetting the V-A escape interval. The ARP (atrial refractory period) extends from the beginning of the SAV (Sensed AV) or PAV(Paced AV) interval following either an A-EVENT or an A-TRIG and until a predetermined time following a V-EVENT or a V-TRIG as a post-ventricular atrial refractory period (PVARP). A ventricular refractory period (VRP) may also be timed out after a V-EVENT or V-TRIG. The durations of the ARP, PVARP and VRP may also be selected as programmable parameters stored in the microcomputer 302. Controller/timer circuit 330 also controls sensitivity settings of the atrial and ventricular sense amplifiers 360 by means of sensitivity control 350.

The activity sensor 316 (when present) may be coupled to the implantable pulse generator housing 118 and may be a piezoelectric crystal transducer (or other activity sensors could be used as are well known in the art) and its output signal is processed and used as a rate control parameter (RCP). If the IPG 100 is programmed to a rate responsive mode, the patient's activity level developed in the patient activity circuit (PAS) 322 is monitored periodically, and the sensor derived V-A escape interval can be adjusted proportionally to follow the patient's activity. A timed interrupt, e.g., every two seconds, may be provided in order to allow the microprocessor 304 to analyze the output of the activity circuit PAS 322 and update the basic V-A (or A-A or V-V) escape interval employed in the pacing cycle.

In accordance with a preferred embodiment of the present invention, an AS system generator 390 is also coupled with the atrial and ventricular leads 116 and 114 and the can electrode 118 and/or to alternative AS lead systems described below and is triggered into operation by A-GEN and/or V-GEN trigger signals that are used to initiate delevery of AS pulses. Suitable isolation and protection circuits are incorporated within AS system generator 390, output amplifier circuit 340 and the sense amplifiers 360 to isolate each from the other. In operation of the AS system generator 390, the microprocessor 304 also defines fixed or variable AS delay and delivery intervals from pace of sense events as shown in tracings (d) and (e) of FIG. 2A for use by AS delay and delivery interval timers 366 as well as the characteristics of the AS system stimulation for hyperpolarization pulses as shown in tracings (f)–(i) of FIG. 2A. The time-out of the AS delay interval from a preceding A-SENSE or A-PACE event, in an atrial single chamber system or operating mode (FIG. 2B), or a V-SENSE or V-PACE, in a ventricular single chamber or dual chamber system or operating mode, is carried out by the AS delay interval timer. Depending on the configuration or operating mode, the A-GEN and/or V-GEN signal triggers operation of the AS system generator 390 to apply the AS system's pulses between the respective sets of atrial and/or ventricular electrodes during the AS system's pulses delivery interval. As described above in reference to FIGS. 2A–C, the durations of the AS delay and delivery intervals may be correlated to the current escape interval.

Where the AS pulses are delivered to the atrial chamber (s), the device may be primarily used to counter ahhrythmic conditions in the atrial tissue rather than to make it easier to pace in the atrium. Ventricular application of AS pulses are generally of benefit beccause they allow the ventricular tissue to relax more completely before being depolarized and therefore will probably mostly be used to improve the underlying tissue health and to promote better filling and better hemodynamic performance. Appropriate adjustments in the characteristics of the AS pulses can provide both benefits to both chambers.

An optimum AS delay interval may be derived in accordance with a further aspect of the present invention from the sensed pressure signal from the pressure sensor 160. Before describing the algorithm for deriving the optimum AS delay and delivery intervals to optimize cardiac function, attention is directed to FIGS. 5 and 6 which depict a functional flowchart of an exemplary manner of operating the pacemaker illustrated in FIGS. 3 and 4 in the DDD or DDDR pacing mode and in accordance with the invention. For the sake of simplicity, functional steps corresponding to the provision of refractory and blanking periods have been omitted, to allow for easier understanding of the overall timing operational mode. FIG. 5 also depicts the general operating steps of the invention that may be practiced in an IPG that does not provide pacing therapies or provides more limited single chamber pacing therapies in conjunction with the delivery of the AS therapies of the present invention.

Figure 5:
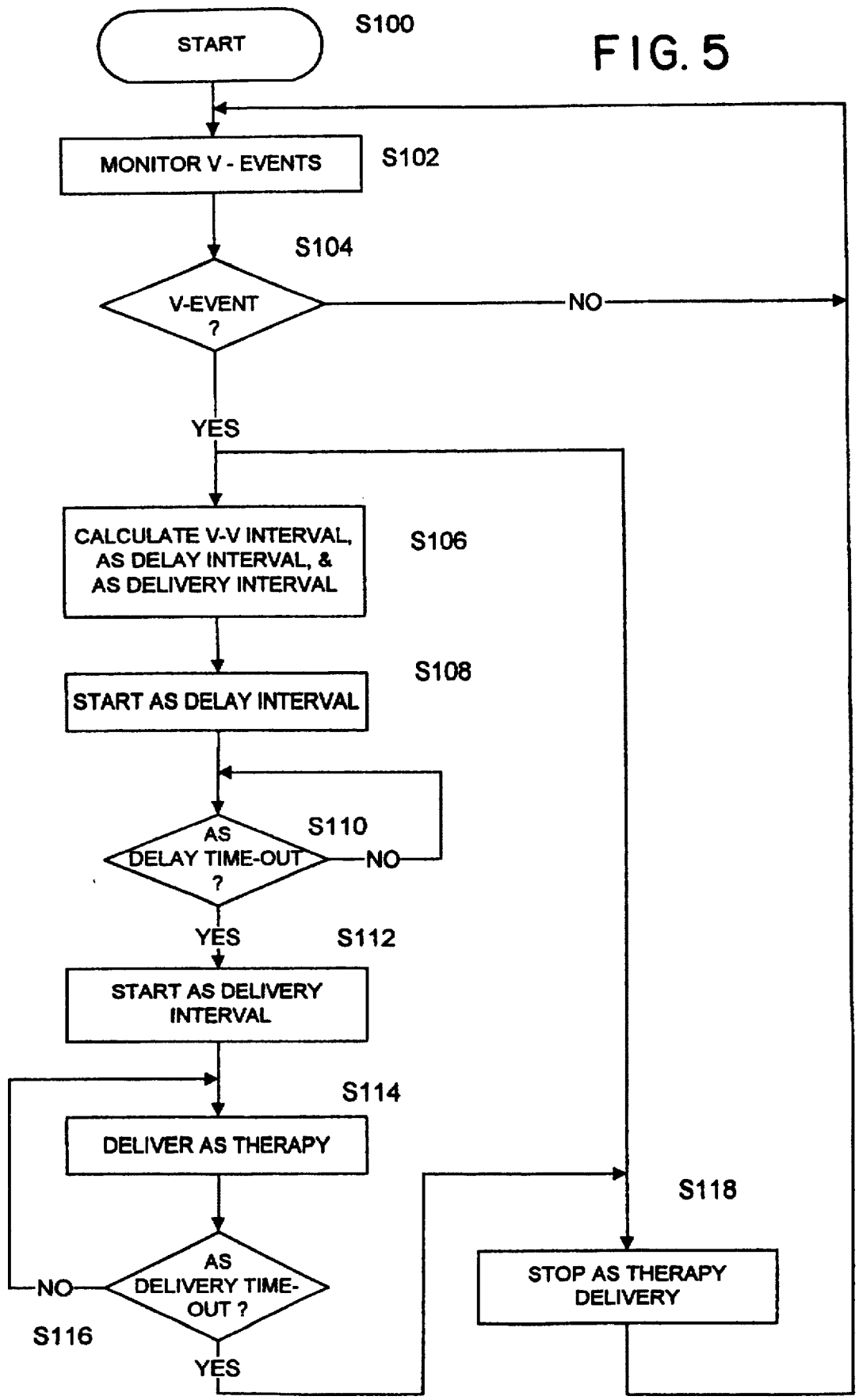
FIG. 5 is a flowchart illustrating the overall steps of practicing the present invention in a preferred embodiment context of a single or dual chamber pacemaker.

In FIG. 5, the general steps of the present invention are depicted in an example providing the delivery of the AS system's pulses during a ventricular escape interval determined by monitoring and averaging interval from any Vevent to the next Vevent (varied as desired to keep or drop paced intervals) on a continuous basis. (For use of this invention in the atrium, obviously the measured interval would be an Atrial event interval.) The general steps of FIG. 5 may be followed in the case where the AS pulses is delivered to the atria or to the ventricles or to both the atria and ventricles. Moreover, it may be employed in a VVI pacemaker or a dual chamber pacemaker or an IPG simply providing AS therapies and capable of sensing V-EVENTs to establish the timing of delivery of the AS pulses. In all cases, it is desirable to ensure that the AS pulse or pulse train is delivered in the appropriate AS delivery time interval after the AS delay time interval as described above with respect to FIGS. 1 and 2.

In step S100, the algorithm is started, that is run by the microcomputer circuit 302 from its memory, and V-EVENTs (and/or V-Paces)are monitored in step S102. The V-EVENTs that occur in step S104 are used in step S106 to calculate and update an average V-V escape interval and a corresponding AS delay and AS delivery interval to be used for that average V-V escape interval. The occurrence of a V-EVENT may also terminate any delivery of an AS pulse or pulse train. In general, it would be expected that in a typical range of heart beat rates, the AS delay interval would be varied through a relatively narrow range, and the AS delivery interval would be shortened as the average V-V interval shortens and lengthened as the average V-V interval lengthens to a greater extent.

The AS delay interval is then started in step S108, and after it times out in step S110, the AS delivery timer is started in step S112, and the delivery of the AS pulse or pulse train for the AS delivery interval is started in step S114 in response to an A-GEN or V-GEN signal. The pulse characteristics of the AS pulses, including the maximum amplitude, the frequency of pulse train therapies and the ramp-up and ramp-down of the single pulse or pulse train amplitudes as shown in tracings (e)–(i) of FIG. 2 are all controlled during step S114 in accordance with AS system's pulses characteristic control signals supplied on bus 392 of FIG. 4 from AS system characteristics register 368. The timing characteristics of the AS system, including the AS delay interval and the AS delivery interval are controlled by the A-GEN or V-GEN timing signals delivered from the AS delivery and delay interval timers 366. The pulse and timing characteristics are collectively referred to as AS system characteristics and are ultimately defined in microcomputer circuit 302 from programmed-in base characteristic settings as optimized in accordance with the steps set forth in FIGS. 7 and 8, described below.

When the AS delivery timer times out in step S 116, the delivery of the AS pulses is stopped in step S 118. It will be understood that when a premature V-EVENT occurs, any AS delay interval or AS delivery interval and any associated AS pulse or pulse train that is timing out or being delivered in steps S108–S118 will be terminated.

Figure 6:
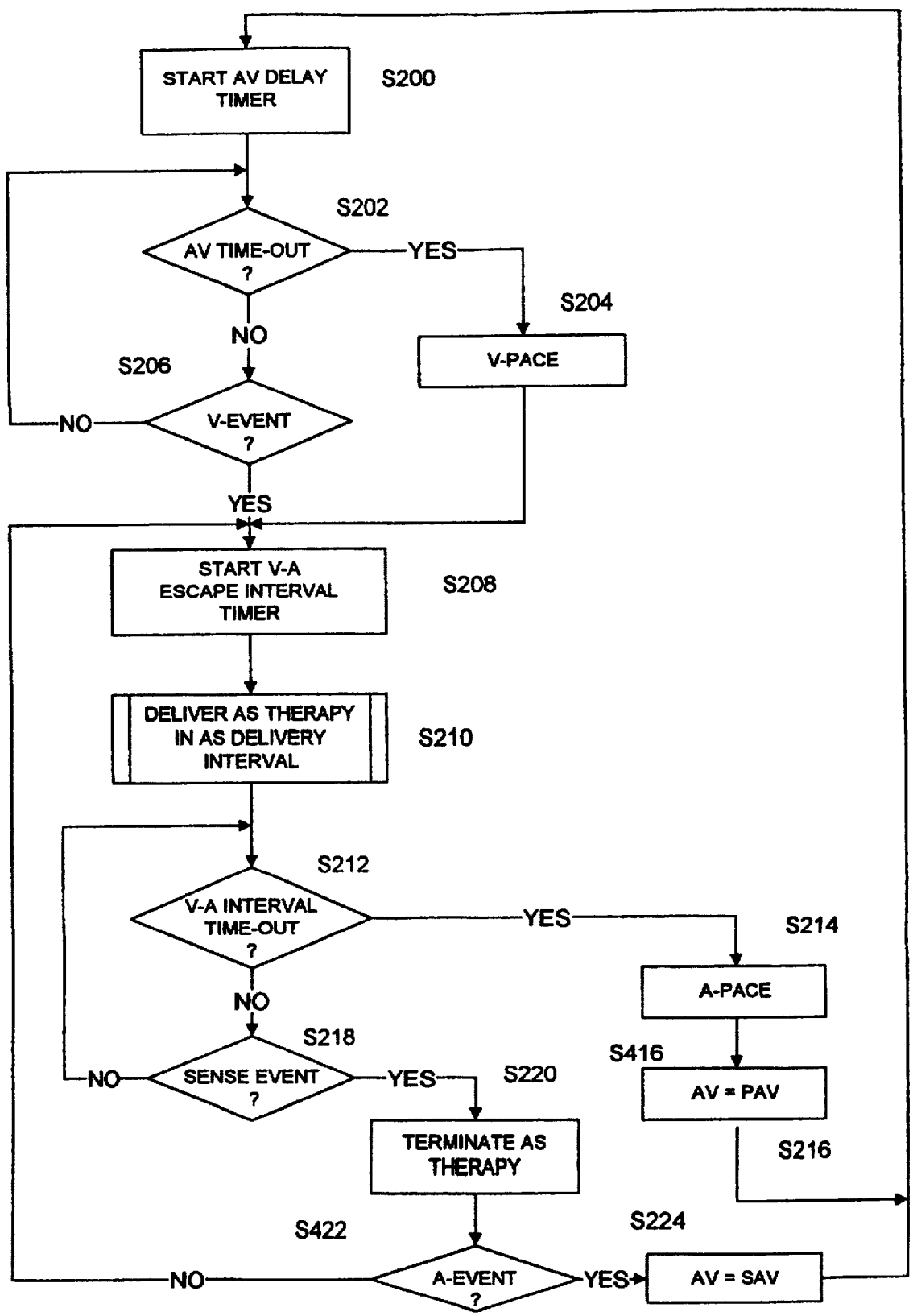
FIG. 6 is a detailed flowchart of a preferred method of practicing the present invention in the context of the exemplary system of FIGS. 3 and 4 using certain of the steps of FIG. 5.

Turning to the flowchart of FIG. 6, the operation of the DDD IPG 300 of FIG. 4 is illustrated wherein the basic timing of the AS pulse or pulse train delivery depends of the definition of an escape interval (an A-A or V-A interval) which may be a fixed lower rate or may vary as a result of the output of an RCP(s) in a range between a lower rate limit and an upper rate limit. In FIG. 6, at step S200, the atrial escape interval is reset and the current AV delay interval is started, both in response to an atrial event (A-PACE or A-EVENT). At step S202, the AV delay interval time-out is monitored, and the system awaits either time out of the current AV delay interval and the triggering of a V-PACE at step S204 or an earlier V-EVENT at step S206. If a V-EVENT does not occur prior to AV delay interval time out, the V-PACE is generated at step S204. When a V-EVENT occurs at step S206 or a V-PACE occurs at step S204, the V-A time interval is started at step S208 to deliver an A-PACE at a V-A escape interval thereafter equal to the overall A-A escape interval (determined by the RCP if present) minus the current AV delay interval. The AS pulse or pulse train is delivered during the delivery interval within the V-A delay interval at step S210 in accordance with the timing diagram of FIG. 2 and following steps S106–S118 of FIG. 5, described above.

During time-out of the AS delay and AS delivery intervals in step S210, the system monitors for subsequent A-EVENTs or V-EVENTS as the V-A escape interval continues to simultaneously time-out at step S212. If a non-refractory SENSE event is declared at step S218 prior to the expiration of the V-A escape interval, the AS pulse or pulse train delivery is terminated (if it is being delivered) or prevented from being delivered at step S220. At step S222, it is determined whether the EVENT is an A-SENSE event. If it is an A-SENSE event, then the AV delay is set to a sensed AV delay (SAV) in step S224. If it is not an A-SENSE, then, it is a V-EVENT that re-starts the V-A escape interval timer at step S208. If the V-A escape interval expires at step S212 without an A-EVENT or V-EVENT, an A-PACE pulse is generated at step S214. The next succeeding AV delay interval is defined to be equal to a paced AV (PAV) delay at step S216, followed by reset of the V-A escape interval and the AV delay interval at step S200. In this manner, the AS pulse or pulse train is delivered during the V-A interval in this example.

Figure 7:
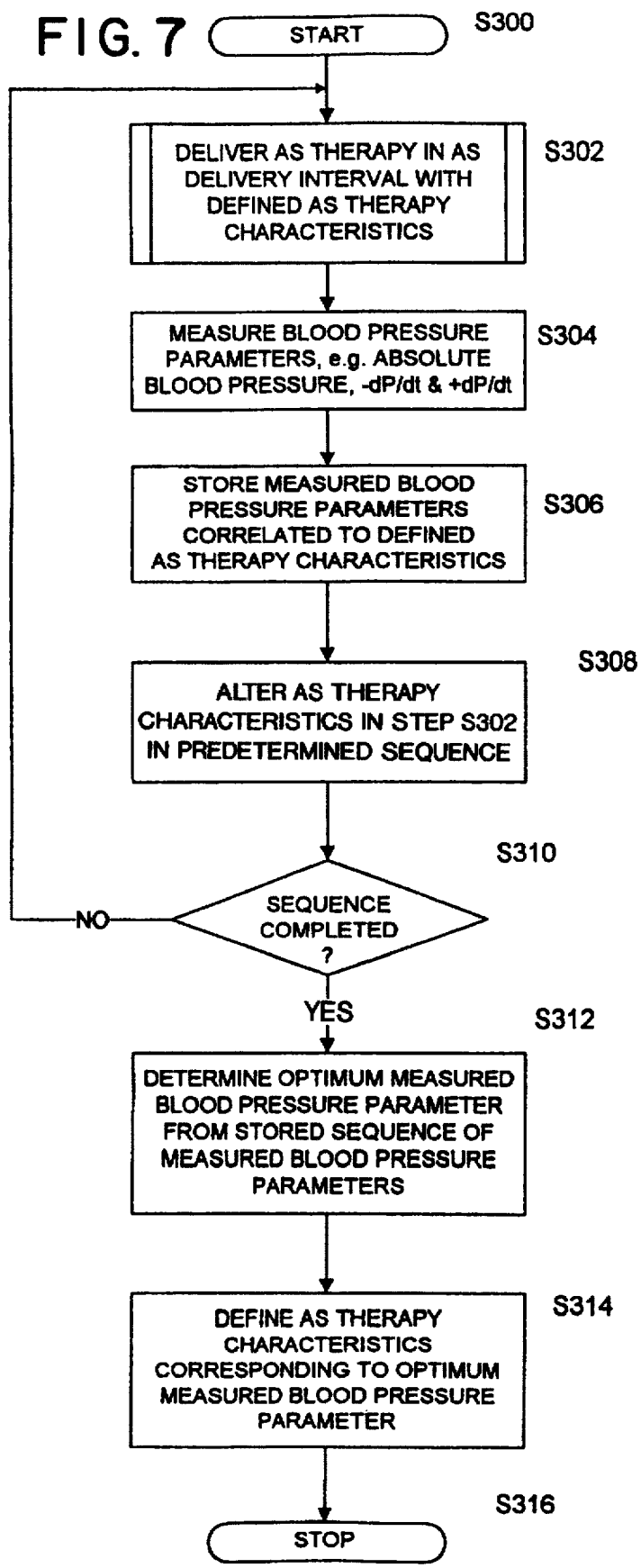
FIG. 7 is a flowchart of the steps of effecting the initial optimization of the AS system characteristics as a function of intracardiac blood pressure.
Figure 8:
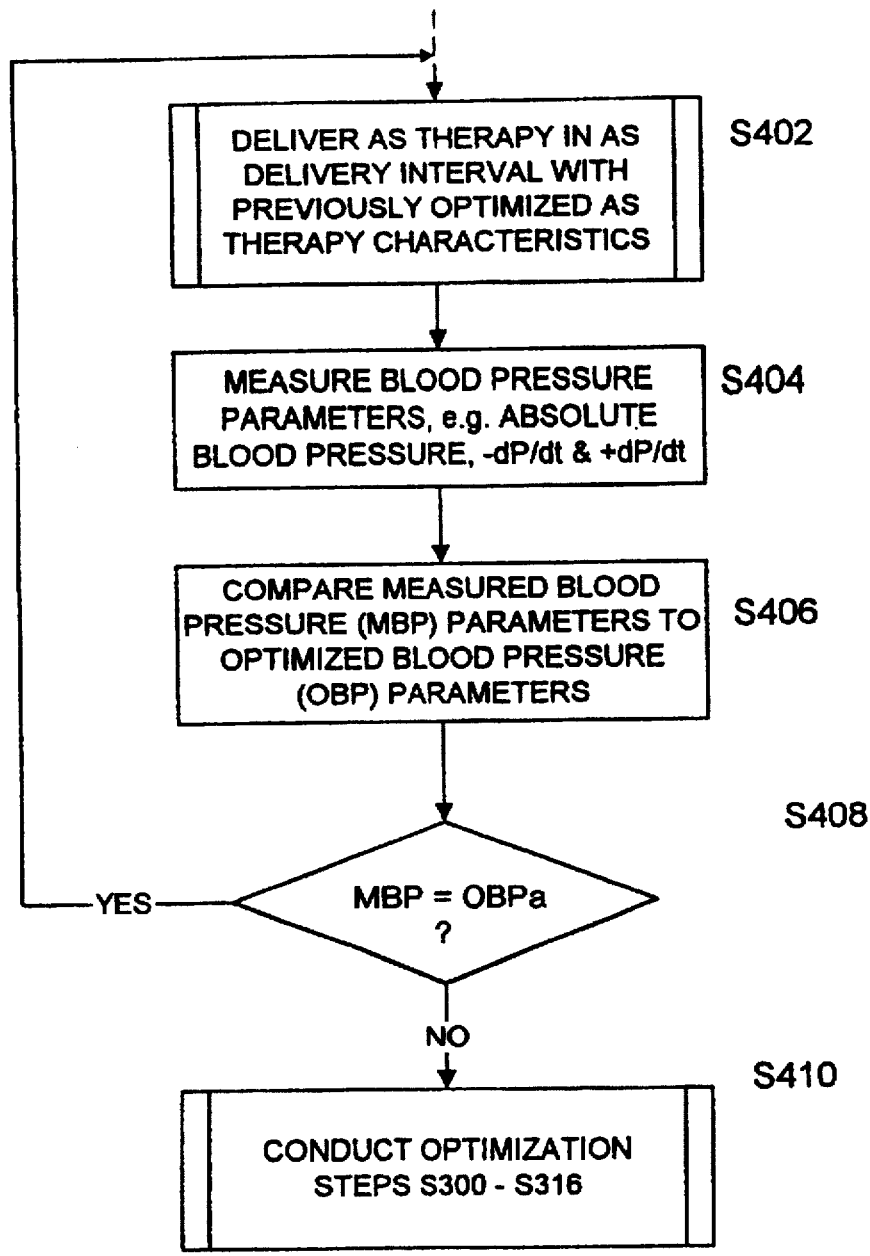
FIG. 8 is a flowchart of the steps of confirming the optimization of the AS system characteristics as a function of intracardiac blood pressure.

In accordance with a further aspect of the present invention, the optimum AS delay and delivery intervals are determined following the steps of the initialization flowchart depicted in FIG. 7 and the confirmation flowchart of FIG. 8 using the RVP (or RAP, if AS pulse or pulse train delivery is to atrial AS electrodes) absolute pressure and/or rate of change pressure signal and the current V-A interval. Assuming that the right ventricular pressure is measured from pressure sensor 160, when the algorithm depicted in the flowchart of FIG. 7 is activated and certain conditions are met, the RVP and preferably the −dP/dt signals are derived by the pressure signal processor 380 and supplied to the digital timer and controller circuit 330.

Referring again to the solid line, left ventricular pressure tracing of FIG. 1, the RVP closely follows that depicted left ventricular pressure waveform, wherein the absolute blood pressure falls rapidly during the isovolumetric relaxation and rapid filling intervals between $T_4$ and until the minimum pressure is reached between $T_5$ and $T_6$. In accordance with this aspect of the present invention, the falling pressure can be differentiated to determine the $-dP/dt^{peak}$ value. A peak detector in controller/timer circuit 330 preferably determines the $-dP/dt^{peak}$ and employs it to measure or sample the corresponding RVP signal amplitude which is digitized in the ADC and multiplexor 328 and employed in the algorithm as described below. These functions of pressure signal processor 380 and a suitable circuit for providing the +dP/dt, −dP/dt and RVP (or RAP) signals are disclosed in detail in commonly assigned U.S. Pat. No. 5,535,752. A suitable absolute pressure sensor that could be used for pressure sensor 160 is disclosed in commonly assigned U.S. Pat. No. 5,564,434 (P-3508) filed in 1996 by Meisel et al., for IMPLANTABLE CAPACITIVE ABSOLUTE PRESSURE AND TEMPERATURE SENSOR, incorporated herein by reference. Circuitry that can be used for powering the absolute pressure sensor and providing a pressure output signal therefrom usable as pressure signal processor 380 is also disclosed in U.S. Pat. No. 5,564,434.

The initialization algorithm of FIG. 7 is commenced typically in a patient work-up conducted by the physician to optimize each of the variable AS pulse or pulse train characteristics in a sequence of adjusting the characteristic, accumulating measured blood pressure values for each adjusted characteristic value in the sequence, comparing the measured blood pressure parameters in the sequence to one another and then selecting the AS pulse or pulse train characteristic providing the optimum blood pressure reading indicative of optimal cardiac function. In step S300, the initialization method is commenced, and the AS pulse or pulse train is delivered in step S302 following the steps of FIG. 5 or FIGS. 5 and 6, depending on the system configuration. The blood pressure parameters are measured in step S304 and stored in step S306 correlated to the current AS system characteristics. In step S308, the particular AS system characteristic under consideration is altered by one incremental value in a defined range between maximum and minimum characteristic values, and steps S302–S308 are repeated with the altered characteristic value if the sequence is not completed as determined in step S310.

The characteristics available for adjustment include pulse width, pulse amplitude, slope of leading and trailing edges of the pulse or pulse trainand the timing of delivery with respect to the particular chamber's last and/or next depolarization event. This last characteristic can be varied by varying the AS delay interval and/or the AS delivery interval. The other characteristics can be varied as is well known in the art.

Figure 2C:
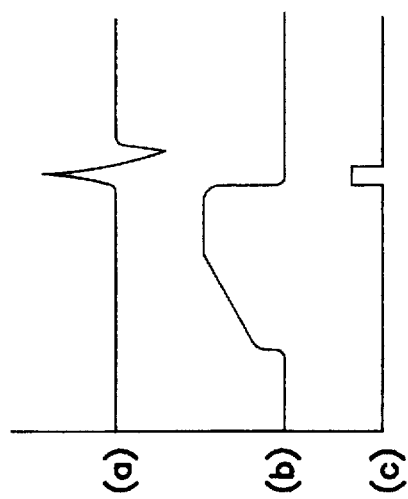
Figure 2B:
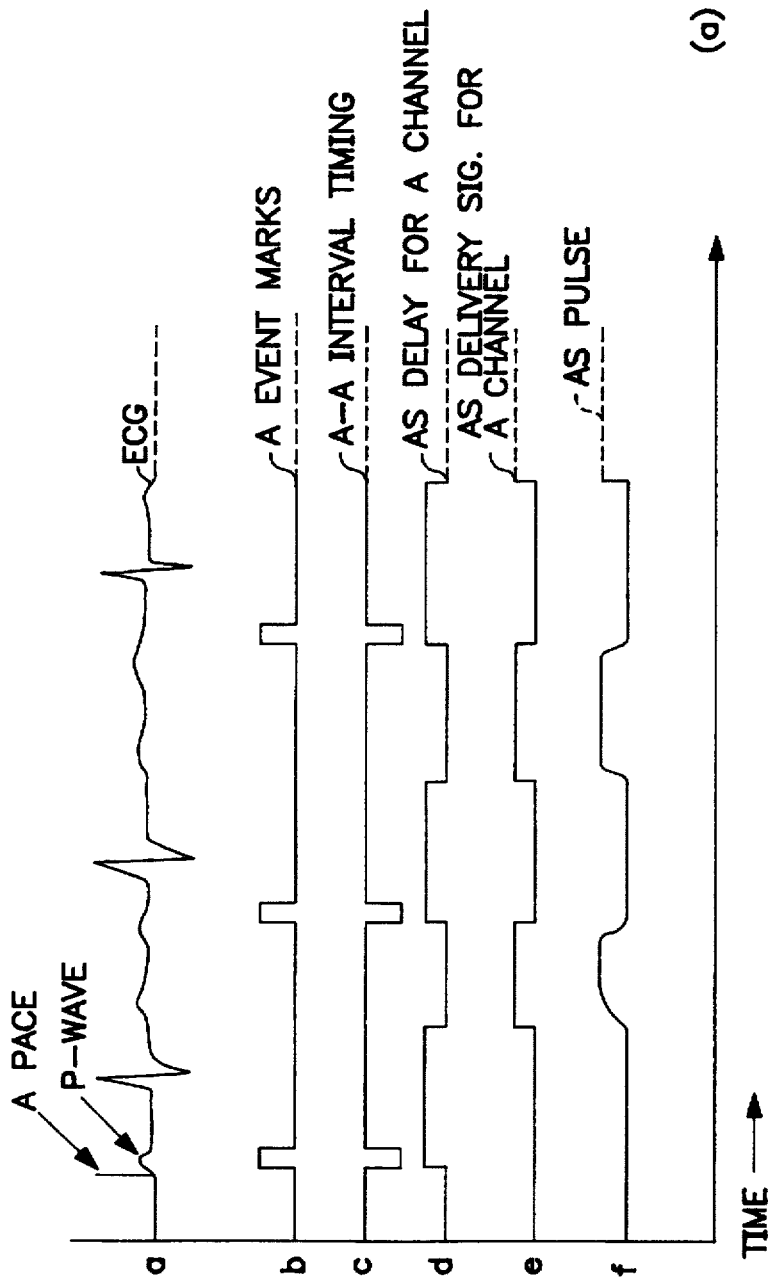

Referring briefly to FIG. 2C, in which the concept of break excitation is illustrated, an anodal pulse waveform, tracing (b), can trigger a myocardial depolarization (QRS of tracing (a)). In the early literature on cardiac pacing it was recognized that a larger pulse energy was required for anodal pacing than for the now universally adopted cathodal pacing waveforms. Accordingly the hyperpolarization waveform may require more energy than a typical pacing pulse, so long as terminating it does not cause break excitation. When there is an excitation sufficient to cause a chamber depolarization (again, here illustrated as the QRS complex in (a)), a sense signal (tracing c) could be generated. If this is too soon after the anodal pulse, adjustments to the AS pulse characteristics should be made. These adjustments should be made concurrently and possibly independently of adjustmentswith adjustments based on pressure or other physiologic parameter being used as described above.

When the sequence is completed in step S312, the optimum measured blood pressure (MBP) parameter is determined from the stored blood pressure parameter values. For example, this may be the highest −dP/dt$^{peak}$ value achieved, indicating optimal relaxation in the heart chamber. In step S314, the AS system characteristic value providing the optimum MBP value is itself stored in memory for use as the AS system defining characteristic value during clinical operation of the system. The determined optimum MBP is itself stored in the microcomputer circuit 302's memory as the optimum blood pressure (OBP) parameter for use in the confirmation algorithm of FIG. 8 during clinical operation of the system.

The optimization algorithm of FIG. 8 may be entered into automatically and continuously or periodically for a time period starting at a programmed-in time of day, for example, as long as the paced or intrinsic heart rhythm is stable. The microcomputer 302 (or a separate timer in the digital controller/timer circuit 330) maintains the time(s) of day and the total optimization time length (in minutes) that the optimization method is enabled. For example, in the system of FIG. 4 operating in accordance with FIGS. 5 and 6, at the specified or programmed-in time of day, the intrinsic heart rate may be monitored to determine if the atrial rate is stable or the intrinsic atrial rate may be overdriven at a shortened atrial escape interval to ensure a stable rate. In this regard, the digital timer/controller circuit 330 includes a stability counter that is responsive to atrial interval timer. The atrial interval timer is started on a V-EVENT or V-TRIG and terminated on an A-TRIG or the next V-SENSE or A-SENSE. Successive V-A intervals are compared to one another and a small delta value defining stability criteria. The count of stability counter is incremented by those atrial intervals satisfying the stability criteria and as long as V-EVENTs do not occur. In a ventricular only system, the same process may be followed to determine a stable ventricular heart rate.

Turning to FIG. 8, it presumes a triggering event is satisfied and at step S402, the AS is being delivered in accordance with the steps of FIGS. 5 and 6. At step S404, the blood pressure parameters are measured during delivery of the AS stimulation pulses. The MBP values are compared to the OBP values stored in memory in step S406. In this regard, an OBP range may be defined as OBP$_R$ in step S406 to allow for insignificant fluctuations in the current MBP with time, and the current MBP compared with OBP$_R$ in step S408. If the current MBP is outside the range defined by OBT$_R$, then the optimization steps S300–S316 may be conducted automatically by the microcomputer circuit 302. In this case, all or only a selected number of characteristics may be re-tested to derive new AS stimulation pulses' characteristics. For example, only the AS delay interval and the AS delivery interval may be re-tested. Alternatively, the event may be stored in memory with an appropriate date stamp for subsequent interrogation by the physician at a scheduled patient follow-up visit. If the situation persists, the physician may initiate and monitor the operation of the optimization algorithm of FIG. 7 to derive an optimum set of AS stimulation pulses' characteristics.

In this manner, the AS stimulation pulses' characteristics are preferably optimized in an initialization process that determines the AS stimulation pulses' characteristics that provide the optimum blood pressure parameters and thereafter continually or from time to time in a confirmation process. The confirmation of the AS stimulation pulses' (or system) characteristics is determined by measuring one or more blood pressure parameter in the right ventricle reflecting the blood pressure in the heart chamber subjected to the AS and comparing the measured blood pressure parameter to the corresponding optimum blood pressure parameter determined in the initialization process. The initialization process is repeated if the comparison shows a deterioration in cardiac function response to the AS.

In the system of FIG. 4, the two pacing tip and ring electrodes of standard endocardial atrial and ventricular leads 116 and 114 are employed to provide four anodal stimulation sites in the atrial and ventricular chambers 12 and 16. Depending on placement, the ring electrodes 120 and 128 may not be in direct contact with myocardial cells. The extent of the hyperpolarization of myocardial cells may be limited to the apex of the heart and the region of the septum of the atria, the actual extent also affected by the virtual electrode phenomenon.

Therefore, it is contemplated that additional or alternative electrodes and leads may be substituted for the atrial and ventricular bipolar electrodes depicted in FIGS. 3 and 4 or added to the system of FIG. 4 in order to provide a greater surface area of electrode-tissue contact with myocardial cells. A wide variety of distributed electrodes have been disclosed in the prior art for distributing electrodes against the endocardial surface of a heart chamber that may also be used to deliver the AS therapies over a wide area of the heart. Other AS system delivery electrodes usable in the various embodiments and variations of the invention include the endocardial and epicardial cardioversion and pace/sense electrodes of all types known in the art. It is preferable that the AS delivery electrodes contact the heart chamber endocardium or epicardium either at multiple sites or over substantial areas so that myocardial cells in contact with or in the vicinity of the electrodes become hyperpolarized due to the AS system and so the area affected is large. A number of different approaches may be followed to accomplish this distribution of delivery, for example, the distributed electrode systems disclosed in U.S. Pat. No. 5,181,111 and in commonly assigned co-pending U.S. patent application Ser. No. 08/507,699 now U.S. Pat. No. 5,657,914 filed 17 Jan., 1996, Williams et al., for MULTI-ELECTRODE, UNIFORM FIELD, INTRACARDIAC DEFIBRILLATION LEADS, both incorporated herein by reference, may be advantageously employed. Similarly, epicardial patch cardioversion electrodes of the types shown in U.S. Pat. Nos. 4,821,723, 5,087,243 and 5,243,978, incorporated herein by reference, may be employed in either atrial and/or ventricular locations. Other large surface area endocardial cardioversion electrodes are disclosed, for example, in U.S. Pat. Nos. 5,433,729 and 5,509,925, and International Patent Publication No. WO 96/0585 (P-3023) filed in the United States in July 1994, all incorporated herein by reference.

Figure 9:
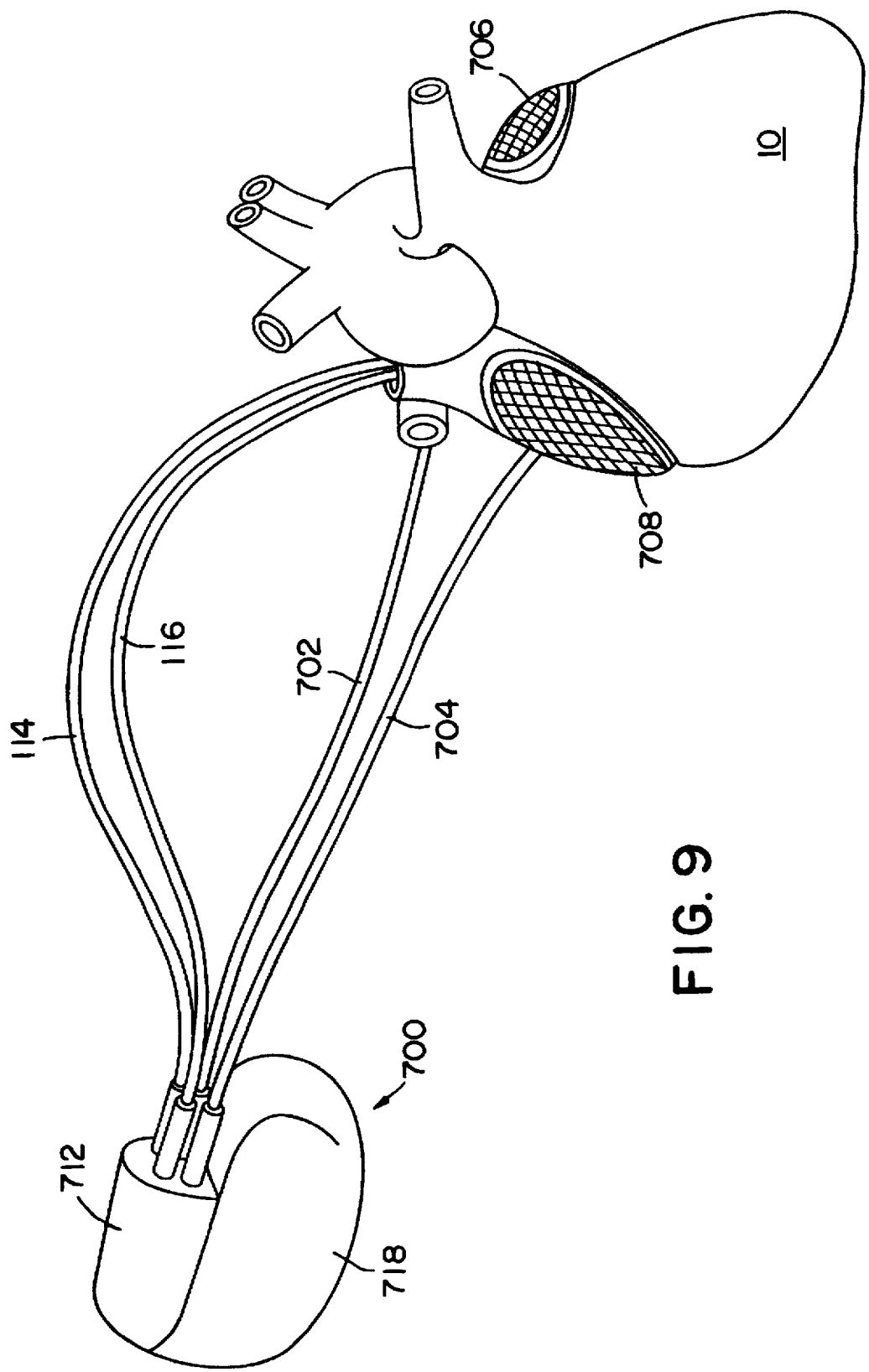
FIGS. 9–15 are views illustrating exemplary alternative embodiments of AS system delivery electrodes usable in the system of FIG. 4 for delivering AS pulses over large areas of the heart or a selected heart chamber.
Figure 10:
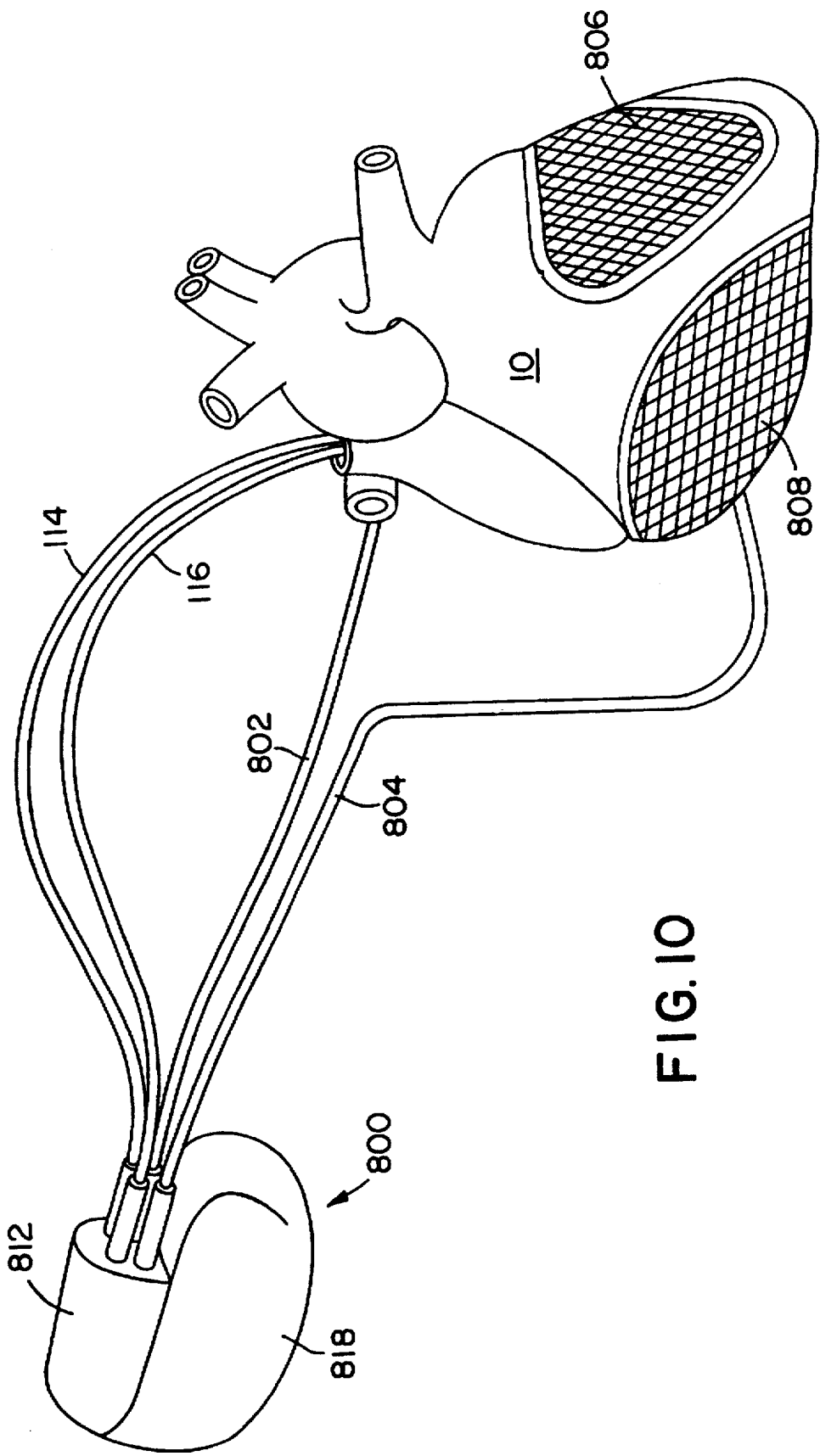

For example, FIG. 9 depicts an atrial system using a modified IPG 700 coupled with atrial epicardial leads 702 and 704 that terminate in large surface area atrial patch electrodes 706 and 708. AS therapies may be delivered between the can electrode 718 and the atrial patch electrodes 706 and 708 or between the atrial patch electrodes 706 and 708 and one or more endocardial electrodes coupled to leads 114 and 116. Similarly, FIG. 10 depicts a ventricular system using a similar modified IPG 800 coupled with ventricular epicardial leads 802 and 804 that terminate in large surface area ventricular patch electrodes 806 and 808. AS therapies may be delivered between the can electrode 818 and the ventricular patch electrodes 806 and 808 or between the ventricular patch electrodes 806 and 808 and one or more endocardial electrodes coupled to leads 114 and 116. In either case, only one endocardial lead 114 or 116 may be provided and only one patch electrode and lead may be used in a given system. Moreover, one or more atrial and ventricular patch leads and electrodes may be combined in the same system as shown for example in U.S. Pat. Nos. 4,821,723 and 5,243,978.

Figure 11:
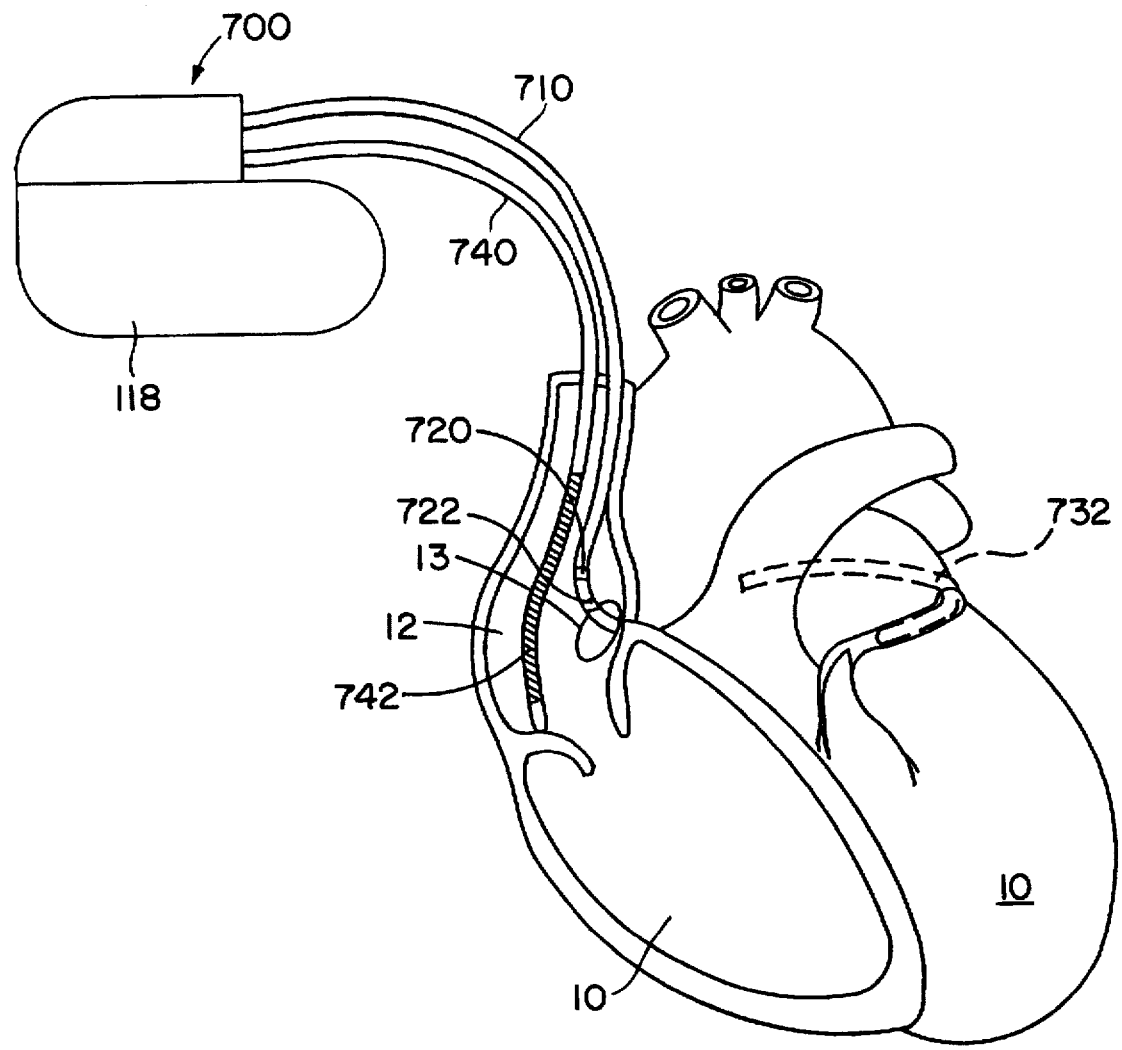
Figure 12:
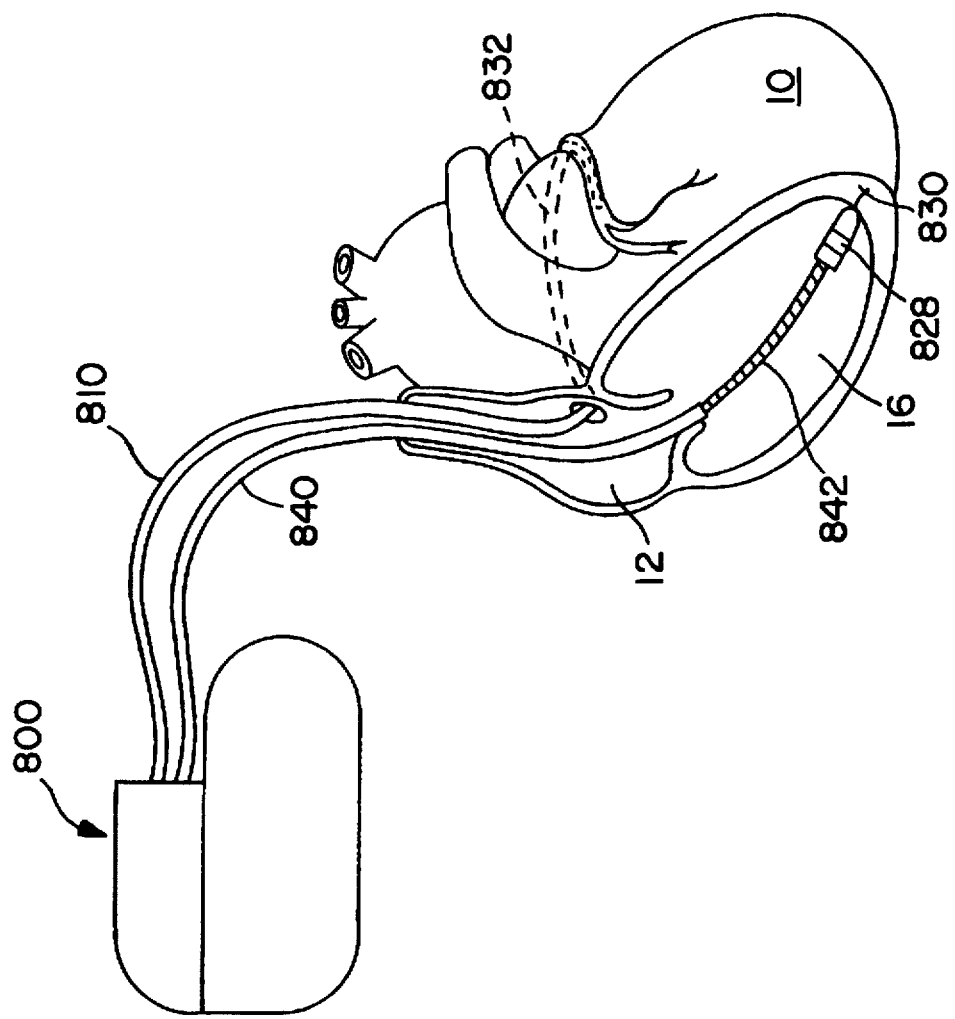

Similarly, endocardial leads having large surface area AS electrodes may be employed separately or in conjunction with pacing and sensing leads of the type depicted in FIG. 3 and/or in conjunction with atrial and/or ventricular epicardial patch AS electrodes of the type depicted in FIGS. 9 and 10. FIGS. 11 and 12 depict atrial and ventricular embodiments of systems using endocardial leads bearing elongated, exposed AS electrodes for increasing contact with atrial and ventricular myocardium. Alternatively, the AS electrodes described below may be formed of a series of spaced apart ring electrodes rather than a continuous elongated electrode.

Such an atrial lead system combining pace/sense electrodes and an elongated large surface area electrode of the type described in U.S. Pat. No. 5,165,403 for use in atrial cardioversion/defibrillation is depicted in FIG. 11. The atrial IPG 700 is coupled to a coronary sinus lead 710 bearing an elongated AS electrode 732 lodged in the great vein and coronary sinus and a pair of ring electrodes 720 and 722 for atrial sensing and pacing, A further atrial lead 740 is depicted bearing a further elongated AS electrode 742 lodged in the right atrium 12 and extending proximally through opening 13 toward the superior vena cava. The further AS electrode 742 may be coiled within the atrial chamber and may also extend into the ventricle. However, it should not contact the pace/sense electrodes 720 and 722. For that reason, the pace/sense electrodes 720, 722 may be formed at the end of the further atrial lead 740 with a fixation mechanism for being fixed in the atrial appendage in a manner well known in the art. AS therapies are delivered between the AS electrodes 732, 742 and the can electrode 718 or other return electrode.

In the electrode system of FIG. 11, an additional lead extending into the ventricle with ventricular sense electrodes of the type shown in FIG. 4 may be needed to conduct V-SENSE signals. Alternatively, the V-SENSE signals from the far-field ventricular electrogram may be detected from the CS electrodes and employed in synchronizing the delivery of the atrial AS therapies.

A ventricular lead system similar to that disclosed in U.S. Pat. No. 5,312,441 for use in ventricular cardioversion/defibrillation is depicted in FIG. 12. The ventricular IPG 800 is coupled to a further coronary sinus lead 810 bearing an elongated AS electrode 832 lodged deep in the great vein and coronary sinus and optionally extending toward the ventricular apex into the great or middle cardiac vein. A further ventricular lead 840 is depicted bearing a further elongated AS electrode 842 lodged in the right ventricle and having a pair of ventricular pace/sense electrodes 828 and 830 fixed in the ventricular apex. The further AS electrode 842 may be coiled within the ventricular chamber 16 and may also extend into the atrial chamber 12. However, it should not contact the pace/sense electrodes 828 and 830. Again, for that reason, the pace/sense electrodes 828, 830 are lodged deep into the trabeculae of the ventricular apex in a manner well known in the art. In this example, AS therapies are delivered between the AS electrodes 832, 842 and the can electrode 818.

Figure 13:
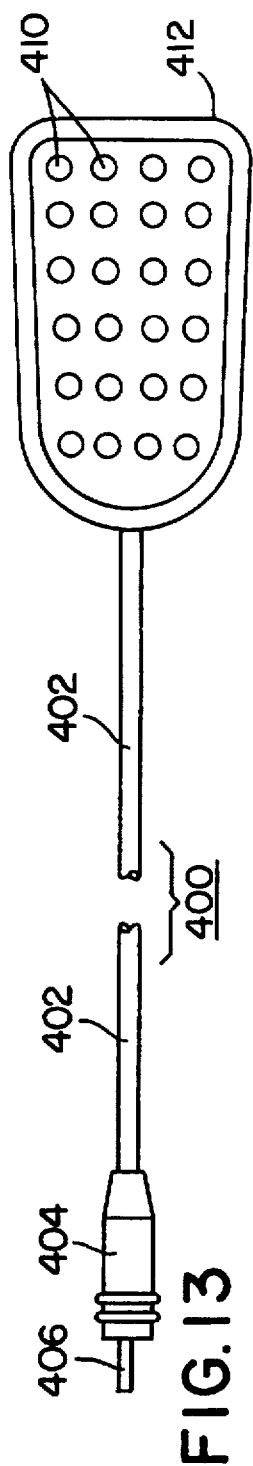

In a further variation, the atrial patch AS electrodes 706, 708 and the ventricular patch AS electrodes 806, 808 may be formed in the manner of lead 400 depicted in FIG. 13 having a plurality of conductive electrode areas 410 arrayed on about a substrate 412. In this instance, all of the electrode areas are electrically connected in common and to a lead conductor within lead body 402 extending to lead connector 404 and terminating in lead connector pin 406. A similar change may be made to the elongated endocardial, atrial and ventricular, AS electrodes 732, 742 of FIG. 11 and 832, 842 of FIG. 12.

Figure 14:
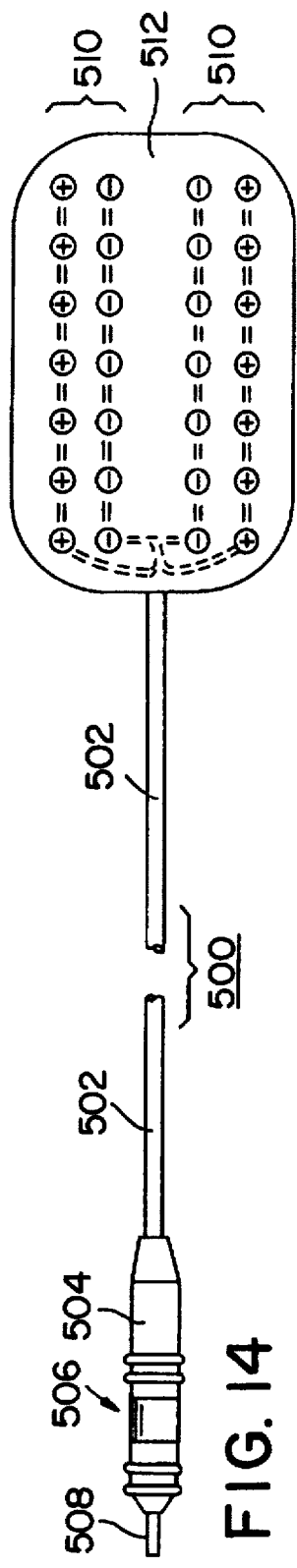

In any of these illustrated embodiments, the return electrode for the delivery of the AS therapies may comprise one or more of the other electrodes in the system or preferably the can electrode 118. In a further epicardial patch variation depicted in FIG. 14, multiple, discrete bipolar electrode areas 510 are substituted for the large surface area patch electrodes of FIGS. 9 and 10. In this variation, discrete positive and return electrode areas 510 are formed on patch substrate 512 in any pattern. The positive area electrodes are electrically connected in common and to a first conductor within lead body 502 that extends to a connector pin 508 of connector 504. Similarly, the negative area electrodes are electrically connected in common and to a second conductor within lead body 502 that extends to a connector ring 506 of connector 504.

Figure 15:
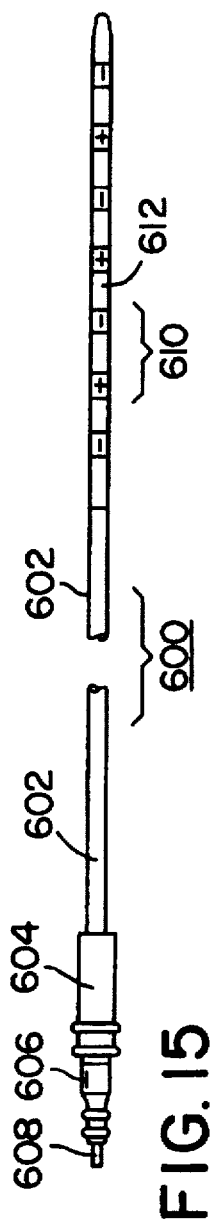

Similarly, in a further endocardial electrode variation depicted in FIG. 15, multiple discrete, ring-shaped bipolar electrodes 610 are formed along the lead body and are substituted for the elongated exposed AS electrodes 732, 742 and 832, 842 of FIGS. 11 and 12. The positive ring-shaped electrodes are electrically connected in common and to a first conductor within lead body 602 that extends to a connector pin 608 of connector 604. Similarly, the negative ring-shaped electrodes are electrically connected in common and to a second conductor within lead body 602 that extends to a connector ring 606 of connector 604.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

What is claimed is:

1. A method of operating a medical device having electrode means adapted for placement about the heart of a living body for hyperpolarizing cardiac cells and characterized by having means to deliver anodal stimulation through said electrode means comprising the steps of:

detecting depolarizations of a chamber of a patient's heart and providing a sense signal in response thereto;

timing an anodal stimulation delivery interval from the sense signal;

generating an anodal stimulation electrical pulse characterized by a waveform having a characteristic sufficient to hyperpolarize myocardial cells of the heart chamber, said waveform also having no characteristic sufficient to capture said cells;

delivering the anodal stimulation therapy to the heart chamber during a delivery interval timed in relation to the sensed signal.

2. The method of claim 1 wherein said timing step further comprises the step of:

establishing a delay interval between the sense signal and the commencement of the anodal stimulation delivery interval such that said anodal stimulation waveform reaches said heart electrode means during an intrinsic relaxation time between depolarizations of the cardiac cells.

3. The method of claim 2 wherein said timing step further comprises the step of:

establishing a delay interval between the sense signal and the commencement of the anodal stimulation delivery interval such that said anodal stimulation waveform reaches said heart electrode means during the intrinsic relaxation time between depolarizations of the cardiac cells that caused the generation of said sense signal.

4. The method of claim 1 wherein said generating step further comprises the step of:

delivering said anodal stimulation pulse waveform such that the waveform comprises a plurality of anodal energy pulses commencing with an initial pulse having an initial pulse energy level and terminating with a terminating pulse having a terminating pulse energy level, and wherein the intervening pulses have energy levels that are increased from said initial pulse energy level to a maximum pulse energy level and decreased from the maximum pulse energy level to said terminating pulse energy level in a manner so as to avoid depolarization of the myocardial cells.

5. The method of claim 1 wherein said generating step further comprises the step of:

establishing an anodal stimulation pulse waveform comprising a plurality of anodal energy pulses commencing with an initial pulse having an initial pulse energy level and terminating with a terminating pulse having a terminating pulse energy level, and wherein the intervening pulses energy levels are decreased from the maximum pulse energy level to said terminating pulse energy level sufficiently to avoid depolarization of the myocardial cells.

6. The method of claim 1 wherein said generating step further comprises the step of:

establishing an anodal stimulation pulse waveform comprising a plurality of anodal energy pulses commencing with an initial pulse having an initial pulse energy and terminating with a terminating pulse having a terminating pulse energy, and wherein the intervening pulses are increased from said initial pulse energy to a maximum pulse energy sufficiently to avoid depolarization of the myocardial cells in response to make excitation effects.

7. The method of claim 1 wherein said generating step further comprises the step of:

establishing an anodal stimulation pulse waveform commencing with an initial pulse energy and terminating with a terminating pulse energy, and wherein the intervening pulse energy is increased from said initial pulse energy to a maximum pulse energy and decreased from the maximum pulse energy to said terminating pulse energy sufficiently to avoid depolarization of the myocardial cells in response to make and break excitation effects.

8. The method of claim 1 wherein said generating step further comprises the step of:

establishing an anodal stimulation pulse waveform commencing with an initial pulse energy and terminating with a terminating pulse energy, and wherein the intervening pulse energy is decreased from the maximum pulse energy to said terminating pulse energy sufficiently to avoid depolarization of the myocardial cells in response to break excitation effects.

9. The method of claim 1 wherein said generating step further comprises the step of:

establishing an anodal stimulation pulse waveform commencing with an initial pulse energy and terminating with a terminating pulse energy, and wherein the intervening pulse energy is increased from said initial pulse energy to a maximum pulse energy sufficiently to avoid depolarization of the myocardial cells in response to make or break excitation effects.

10. The method of claim 1 further comprising the steps of:
   measuring a physiologic function of the body; and modifying the anodal stimulation therapy characteristics to optimize the measured function such that as the steps of claim 1 are iteratively operated, said measured physiologic function converges on a predetermined optimum level of said measured physiologic function.

11. A cardiac pacemaker, having anodal stimulation generating means adapted to deliver anodal stimulation pulses comprising:

timing means for determining the timing of pacing pulses to at least one chamber of a patients heart, sensing means to detect depolarizations of a chamber of a patient's heart and providing a sense signal in response thereto;

escape interval means for maintaining and initiating an escape interval upon delivery of a pacing pulse to the heart chamber or in response to a sense signal and for generating an escape interval time-out signal when one said escape interval times out;

pacing pulse delivery means to provide said pacing pulses to the heart chamber at the time out of one of said pacing escape intervals said pacing pulses being capable of depolarization of the heart chamber;

means for timing an anodal stimulation delivery interval from a sense signal or a pacing pulse;

means for generating an anodal stimulation pulse having pulse characteristics insufficient to elicit a depolarization of myocardial cells of the heart chamber; means for delivering the anodal stimulation pulse to the heart chamber during an anodal stimulation delivery interval.

12. Apparatus for hyperpolarizing cardiac cells employing anodal stimulation comprising:

means for detecting depolarizations of a chamber of a patient's heart and providing a sense signal in response thereto;

means for timing an anodal stimulation delivery interval from the sense signal;

means for generating an anodal stimulation pulse having a characteristic sufficient to hyperpolarize myocardial cells of the heart chamber said stimulation pulse also having no characteristic sufficient to capture said cells;

means for delivering the anodal stimulation pulse to the heart chamber during the delivery interval to effect maximal cardiac relaxation of the myocardial cells of the heart.

13. The apparatus of claim 12 wherein said timing means further comprises:

means for establishing a delay interval between the sense signal and the commencement of the anodal stimulation delivery interval to ensure application of the anodal stimulation therapy during intrinsic relaxation time between depolarizations of the cardiac cells of the heart.

14. The apparatus of claim 12 wherein said generating means further comprises:

means for establishing an anodal stimulation pulse waveform comprising a plurality of anodal energy pulses commencing with an initial pulse having an initial pulse energy and terminating with a terminating pulse having a terminating pulse energy, and wherein the intervening pulses are increased from said initial pulse energy to a maximum pulse energy and decreased from the maximum pulse energy to said terminating pulse energy sufficiently to avoid depolarization of the myocardial cells.

15. The apparatus of claim 12 wherein said delivery means further comprises:

electrode means for delivering said anodal stimulation therapy simultaneously between multiple site electrodes spaced about the heart and a common return electrode.

16. The apparatus of claim 12 wherein said delivery means further comprises:

electrode means for delivering said anodal stimulation therapy between at least one large surface area electrode positioned about the heart and a return electrode.

17. The apparatus of claim 12 wherein said delivery means further comprises:

electrode means for delivering said anodal stimulation therapy simultaneously between multiple site intracardiac electrodes and a common return electrode.

18. The apparatus of claim 12 wherein said delivery means further comprises:

electrode means for delivering said anodal stimulation therapy between a large surface area intracardiac electrode positioned within the heart or a heart vessel and a return electrode.

19. The apparatus of claim 12 wherein said delivering means further comprises:

electrode means for delivering said anodal stimulation pulse simultaneously between a plurality of closely spaced electrode pairs adjacent the heart chamber.

20. Apparatus as set forth in claim 12 and further comprising means for measuring a physiologic function of the body and generating a value measurement signal responsive thereto; and means for responding to the value of said measurement signal so as to modify the anodal stimulation pulse characteristics to optimize the measured function.

* * * * *